United States Patent
Makino et al.

(10) Patent No.: US 9,538,978 B2
(45) Date of Patent: Jan. 10, 2017

(54) RADIOGRAPHIC IMAGING SYSTEM AND ACCESS CONTROLLER FOR COMMUNICATION ACCESS

(71) Applicant: FUJIFILM Corporation, Tokyo (JP)

(72) Inventors: Kazuhiro Makino, Ashigarakami-gun (JP); Keiji Tsubota, Ashigarakami-gun (JP); Yoshimitsu Kudo, Ashigarakami-gun (JP); Yasunori Ohta, Ahigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 213 days.

(21) Appl. No.: 14/487,865

(22) Filed: Sep. 16, 2014

(65) Prior Publication Data

US 2015/0078522 A1 Mar. 19, 2015

(30) Foreign Application Priority Data

Sep. 17, 2013 (JP) .................................. 2013-192466

(51) Int. Cl.
*A61B 6/00* (2006.01)
*G06F 19/00* (2011.01)

(52) U.S. Cl.
CPC ............. *A61B 6/563* (2013.01); *A61B 6/4405* (2013.01); *A61B 6/56* (2013.01); *A61B 6/566* (2013.01);
(Continued)

(58) Field of Classification Search
CPC ... A61B 6/4233; A61B 6/4283; A61B 6/4405; A61B 6/54; A61B 6/542; A61B 6/545; A61B 6/548; A61B 6/56; A61B 6/563; A61B 6/566
(Continued)

(56) References Cited

U.S. PATENT DOCUMENTS 7,545,914 B2 * 6/2009 Kito ..................... A61B 6/4283
378/207
7,561,668 B2 * 7/2009 Ohta ..................... G03B 42/04
378/102

(Continued)

FOREIGN PATENT DOCUMENTS

JP 2005-253627 A 9/2005
JP 2012-34936 A 2/2012

*Primary Examiner* — Allen C. Ho
(74) *Attorney, Agent, or Firm* — Birch, Stewart, Kolasch & Birch, LLP

(57) ABSTRACT

An X-ray imaging system includes an X-ray imaging apparatus and an access controller, which controls communication access of the X-ray imaging apparatus having an electronic cassette for forming an X-ray image and wirelessly transmitting the X-ray image. Before the electronic cassette starts transmitting the X-ray image, a priority request signal for priority of the first radio communication channel to the electronic cassette over a portable terminal device of radio communication is received. Upon receiving the priority request signal, presence of the portable terminal device is checked, in which a radio communication channel of overlap of frequency on the first radio communication channel is used. In presence of the portable terminal device with the overlap, the portable terminal device is regulated in communication regulation while the electronic cassette transmits the X-ray image. Also, the X-ray imaging apparatus is communicable by use of a communication network in wireless communication connection.

20 Claims, 28 Drawing Sheets

(52) U.S. Cl.
CPC ......... *G06F 19/3406* (2013.01); *A61B 6/4233* (2013.01); *A61B 6/4283* (2013.01); *A61B 6/548* (2013.01)

(58) Field of Classification Search
USPC .................................................. 378/62, 91
See application file for complete search history.

(56) References Cited

U.S. PATENT DOCUMENTS

| | | | | |
|---|---|---|---|---|
| 7,593,507 B2* | 9/2009 | Ohta | ................... | A61B 6/032 378/207 |
| 7,712,959 B2* | 5/2010 | Tanabe | ................... | H01J 31/49 250/370.08 |
| 7,737,427 B2* | 6/2010 | Kito | ................... | A61B 6/4233 250/370.08 |
| 7,764,765 B2* | 7/2010 | Ohta | ................... | A61B 6/4233 250/370.09 |
| 7,787,594 B2* | 8/2010 | Ohta | ................... | A61B 6/4233 378/114 |
| 7,864,923 B2* | 1/2011 | Ohta | ................... | G03B 42/04 250/370.09 |
| 7,894,575 B2* | 2/2011 | Tsubota | ................ | A61B 6/548 378/96 |
| 7,896,547 B2* | 3/2011 | Kito | ................... | A61B 6/4283 378/205 |
| 7,974,382 B2* | 7/2011 | Kitano | ................... | G01N 23/04 378/114 |
| 7,991,119 B2* | 8/2011 | Yoshida | ................... | G01T 1/00 378/114 |
| 8,021,047 B2* | 9/2011 | Yoshida | ................ | A61B 6/4035 378/114 |
| 8,053,727 B2* | 11/2011 | Nishino | ................... | A61B 6/56 250/336.1 |
| 8,130,909 B2* | 3/2012 | Nishino | ............... | A61B 6/4283 250/370.09 |
| 8,194,823 B2* | 6/2012 | Ohta | ................... | A61B 6/4233 250/370.09 |
| 8,203,446 B2* | 6/2012 | Tsubota | ................ | H04W 48/02 340/539.1 |
| 8,229,202 B2* | 7/2012 | Kito | ................... | A61B 6/00 378/114 |
| 8,259,904 B2* | 9/2012 | Tsubota | ................... | A61B 6/00 378/116 |
| 8,330,597 B2* | 12/2012 | Nishino | ................... | A61B 6/00 250/370.01 |
| 8,345,820 B2* | 1/2013 | Yoshida | ................ | G03B 42/04 250/370.09 |
| 8,358,740 B2* | 1/2013 | Nakatsugawa | ........ | A61B 6/102 378/116 |
| 8,363,786 B2* | 1/2013 | Nakatsugawa | ...... | A61B 6/4441 378/116 |
| 8,546,777 B2* | 10/2013 | Utsunomiya | ........ | A61B 6/4283 250/580 |
| 8,552,392 B2* | 10/2013 | Kito | ................... | G03B 42/04 250/370.09 |
| 8,576,087 B2* | 11/2013 | Kamiya | ............... | A61B 6/4283 250/318 |
| 8,704,188 B2* | 4/2014 | Kitano | ................... | A61B 6/548 250/370.09 |
| 8,731,141 B2* | 5/2014 | Kuwabara | ............... | A61B 6/00 378/116 |
| 8,798,235 B2* | 8/2014 | Ohta | ................... | G01N 23/04 250/370.09 |
| 8,855,691 B2* | 10/2014 | Kamiya | ............... | A61B 6/4283 340/2.1 |
| 8,929,510 B2* | 1/2015 | Nishino | ............... | A61B 6/4216 378/102 |
| 8,983,035 B2* | 3/2015 | Noma | ................... | H05G 1/64 250/214 DC |
| 9,001,972 B2* | 4/2015 | Takahashi | ................ | H05G 1/30 378/62 |
| 9,168,011 B2* | 10/2015 | Nenoki | ................ | A61B 6/4405 |
| 9,204,855 B2* | 12/2015 | Tsubota | ................ | A61B 6/563 |

* cited by examiner

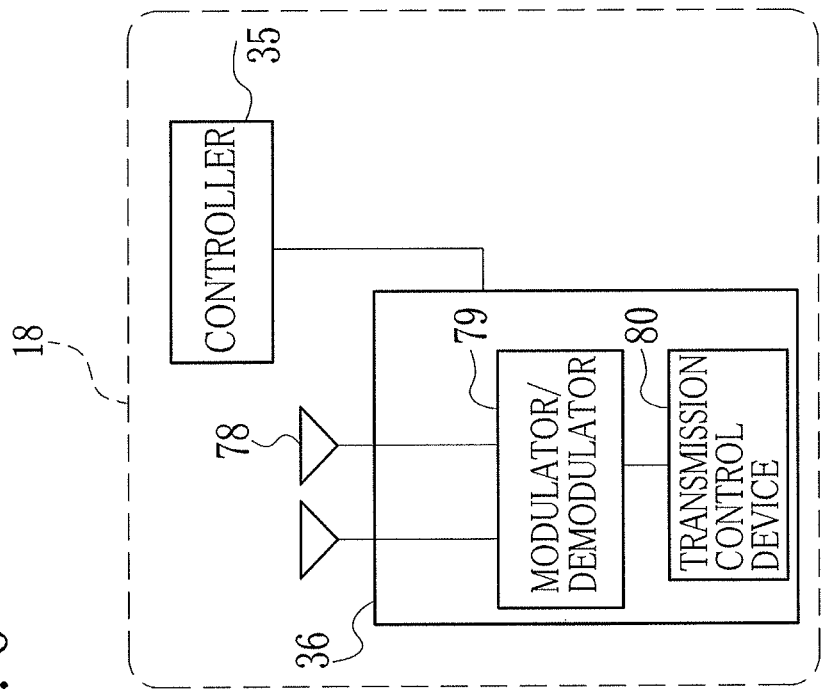
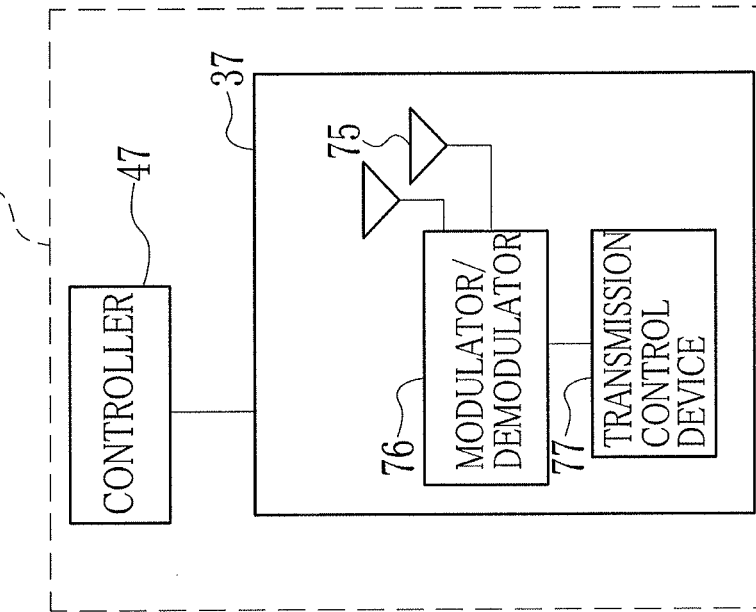
FIG. 6

RADIOGRAPHIC IMAGING SYSTEM AND ACCESS CONTROLLER FOR COMMUNICATION ACCESS

CROSS-REFERENCE TO RELATED APPLICATION

This application claims priority under 35 USC 119 from Japanese Patent Application No. 2013-192466, filed 17 Sep. 2013, the disclosure of which is incorporated by reference herein.

BACKGROUND OF THE INVENTION

1. Field of the Invention

The present invention relates to a radiographic imaging system and an access controller for communication access. More particularly, the present invention relates to a radiographic imaging system and an access controller for communication access, in which radio communication is used, and communication errors or delay due to radio interference in wireless communication connection can be prevented.

2. Description Related to the Prior Art

An X-ray imaging system or radiographic imaging system is widely used in medical diagnosis in a hospital. The X-ray imaging system includes an X-ray source apparatus or radiation source apparatus, and an X-ray imaging apparatus or radiographic imaging apparatus. The X-ray source apparatus generates X-rays. The X-ray imaging apparatus forms an X-ray image or radiation image of a body of a patient by receiving X-rays transmitted through the body. The X-ray source apparatus includes an X-ray source, a source driver (controllable) and a start switch. The X-ray source applies X-rays to the body. The source driver drives and controls the X-ray source. The start switch inputs a command signal to the source driver to turn on the X-ray source. The X-ray imaging apparatus includes an X-ray image detector or radiation image detector, and a console unit, which receives a command signal for the X-ray image detector and the X-ray image from the X-ray image detector, and displays the X-ray image.

The X-ray image detector has a sensor panel or a flat panel detector (FPD), and detects the X-ray image by converting X-rays transmitted though a body into an electric signal. The X-ray image detector transmits the X-ray image immediately to the console unit which operates for displaying an image visibly. The use of the X-ray image detector is highly advantageous over radiography with an X-ray film or IP cassette (imaging plate cassette), because the image can be checked shortly after the imaging.

Examples of X-ray image detectors include a stationary type installed in an examination room, and a portable type, which is an electronic cassette having a portable housing and the sensor panel contained in the portable housing. The electronic cassette is usable in a state fixedly positioned on a floor stand or the like in the examination room for imaging the body in an erect posture or supine posture. Also, the electronic cassette is useful in X-ray imaging of in-patient care in which an operator goes to a hospital room of a patient of limited mobility, namely in a condition without possibility of moving to the examination room.

JP-A 2012-034936 discloses the X-ray imaging apparatus of a type of wireless communication connection between the electronic cassette and the console unit for transmitting data including the X-ray image. There are various modes of positioning the electronic cassette according to body parts of interest in the body. The electronic cassette may be disposed between the body and a bed, or may be held by hands of the patient. It is unnecessary to connect a cable to the electronic cassette by use of the wireless communication connection, so that the positioning of the electronic cassette can be freely carried out without consideration of a path of the cable. However, attenuation of radio waves may be more remarkable assuming that a relative position of the electronic cassette changes according to a distance or direction of the electronic cassette relative to the console unit with changes of the posture and position. Communication quality cannot be stably maintained due to frequent occurrence of communication errors or delay. In view of this, the X-ray imaging apparatus of JP-A 2012-034936 finely changes an output of the communication according to changes in the relative position between the electronic cassette and the console unit, to maintain communication quality stably.

Also, JP-A 2005-253627 discloses a method of ensuring communication quality of an X-ray imaging apparatus in a stable form in a manner similar to JP-A 2012-034936. In a computed tomography apparatus (CT apparatus) of X-rays, there are an image detector for detecting an X-ray image and an image receiver for receiving the X-ray image from the image detector. A radio communication between the image detector and the image receiver is performed with a plural radio communication channels in a multi-channel form. Assuming that failure such as circuit breakage is detected in a first one of the radio communication channels, the radio communication is changed over to a second one of those operable normally.

The ideas of JP-A 2012-034936 and 2005-253627 for ensuring communication quality are technically important in the field of the X-ray imaging apparatus in consideration of effectively preventing communication errors and delay. According to a research of the medical diagnosis in hospitals, the number of imaging requests for the in-patient care is 20 per day in one hospital facility, and may be increased by 30 as additional urgent requests due to the progress of numerous patients. Only one technician or operator frequently works for imaging in the in-patient care. Thus, a task of 50 or more imaging requests must be performed only by himself or herself in a day. In general, each one event of imaging of the imaging request takes about 5 minutes. The in-patient care is for the purpose of care for patients of limited mobility. Positioning of the body of the patient by an operator for a proper posture of his or her upper body requires much time in relation to a position of the electronic cassette. Thus, the importance of ensuring communication quality of data in a stable manner is considerably high in the severely restricted condition of the medical diagnosis in the hospital facility.

However, new problems have been found recently in relation to the imaging in the in-patient care. Communication quality of data in a stable manner cannot be ensured only by the techniques suggested in JP-A 2012-034936 and 2005-253627.

Introduction of radio network nodes (radio communication devices) has been made recently in medical facilities in a manner similar to general use. The X-ray imaging apparatus and other medical apparatus with a radio network node have been used widely. A portable terminal device of radio communication is a typical example for viewing a medical chart or inputting information in electronic data of diagnostic information. However, available bands of frequency of radio waves is limited. Frequency overlap may occur to create radio interference in case a radio communication channel of an equal frequency is used by a plurality of radio network nodes. The radio interference causes communication errors and delay. As the number of radio communication channels is limited, it is impossible to assign all radio network nodes with radio communication channels of different frequencies without creating radio interference.

The X-ray imaging apparatus is moved from room to room in a hospital facility for the purpose of the in-patient care. Communication environment of the X-ray imaging apparatus is changeable with places and time. Positions and numbers of medical service providers (physicians and nurses) carrying portable terminal devices of radio communication are changed according to the hospital rooms and time. The problem of the radio interference cannot be resolved in the in-patient care even with a countermeasure for preventing radio interference in a limited place. The problem of the radio interference becomes more conspicuous according to an increase in the number of the portable terminal devices. The use of the portable terminal devices will be enlarged in future so as to make the problem more serious. In general, a data size of an X-ray image is large among various data for medical use. The problem must be coped with because of a loss in time due to the radio interference with communication errors or delay.

Search has been made by sampling and interviewing plural operators in the field of radiology. In addition to the problem of much time required for positioning of a body of a patient, manual handling of the electronic cassette is considerably laborious due to its large weight in comparison with an X-ray film, IP cassette or the like in the course of supporting the body of the limited mobility. Furthermore, required efficiency in working in a condition of restriction of the time is combined with muscle fatigue of each operator, to cause serious increase in mental stress. Accordingly, communication errors or delay even with a short period causes a problem of lowering the efficiency of the operator because of loss of time and the like. Solution of the above-described problem of communication errors or delay is essentially important in the field of medical diagnosis.

JP-A 2012-034936 and 2005-253627 do not mention those problems. The techniques disclosed in the documents are related to communication errors or delay due to internal factors in the X-ray imaging apparatus. No solution has been known for problems of communication errors or delay due to radio interference of the X-ray imaging apparatus with other radio network node or the like due to external factors of the X-ray imaging apparatus.

SUMMARY OF THE INVENTION

In view of the foregoing problems, an object of the present invention is to provide a radiographic imaging system and an access controller for communication access, in which radio communication is used, and communication errors or delay due to radio interference in wireless communication connection can be prevented.

In order to achieve the above and other objects and advantages of this invention, a radiographic imaging system is provided, and includes a radiographic imaging apparatus having an electronic cassette for forming a radiation image and wirelessly transmitting the radiation image, and an access controller for controlling communication access of the radiographic imaging apparatus. In the radiographic imaging system, the access controller includes a storage medium for storing frequency information of a frequency of a first radio communication channel used by the electronic cassette for transmitting the radiation image, and of a frequency of a second radio communication channel used by a communication device different from the radiographic imaging apparatus and communicable wirelessly. A command receiver receives a priority request signal for priority of the first radio communication channel to the electronic cassette over the communication device before the electronic cassette starts transmitting the radiation image. An overlap detector refers to the storage medium upon receiving the priority request signal, and checks presence of the communication device in which a radio communication channel of overlap of frequency on the first radio communication channel is used. A communication limiter operates in presence of the communication device with the overlap, and regulates the communication device in communication regulation while the electronic cassette transmits the radiation image.

Preferably, the communication regulation includes at least one of interruption of communication, limitation of a data transfer rate of transfer of data per unit time, and a change in the frequency of the radio communication channel used by the communication device.

Preferably, the access controller further includes a frequency information acquisition device for acquiring the frequency information of the second radio communication channel from the communication device.

Preferably, the communication device is at least one of a portable terminal device and an access point device for connecting the portable terminal device to a communication network by wireless communication connection.

Preferably, the communication limiter controls the access point device for the communication regulation.

Preferably, the frequency information acquisition device acquires the frequency information of the radio communication channel used by the access point device.

Preferably, the radiographic imaging apparatus further includes a console unit for receiving the radiation image from the electronic cassette, displaying the radiation image, and inputting a signal to the electronic cassette.

Preferably, the radiographic imaging apparatus generates the priority request signal to the access controller at a predetermined time point before a start of transmission of the radiation image from the electronic cassette in one event of imaging.

Preferably, the radiographic imaging apparatus is combined with a radiation source apparatus, and the radiation source apparatus includes a radiation source for generating radiation. A start switch turns on and off the radiation source.

Preferably, the radiographic imaging apparatus is communicable with the radiation source apparatus, and the predetermined time point is a time point of receiving a signal of operation of the start switch from the radiation source apparatus.

In another preferred embodiment, the electronic cassette detects a start of irradiation of the radiation source, and the predetermined time point is a time point of detecting the start of the irradiation in the electronic cassette.

In still another preferred embodiment, the predetermined time point is one of a time point of making the electronic cassette ready for imaging, a time point of completion of storing in the electronic cassette for detecting the radiation image, and a time point of manually inputting the priority request signal.

Preferably, the priority request signal includes information of a priority level in relation to priority. The communication limiter performs the communication regulation according to the priority level upon receiving a plurality of the priority request signal.

Preferably, the radiation source apparatus is a mobile radiation source apparatus placed on a mobile cart.

Preferably, the access controller is incorporated in the radiographic imaging apparatus.

Preferably, the radiographic imaging apparatus measures a data transfer rate of the electronic cassette per unit time, and assuming that the data transfer rate is lower than a predetermined threshold, generates the priority request signal.

Preferably, the radiographic imaging apparatus has an intermediate network node for wireless communication connection between the electronic cassette and the console unit, and for wireless communication connection of the electronic cassette and the console unit to a communication network.

Preferably, while the electronic cassette transmits the radiation image, the radiographic imaging apparatus interrupts radio communication other than transmitting the radiation image.

Preferably, the console unit receives an imaging request, and interrupts reception of the imaging request while the electronic cassette transmits the radiation image.

Preferably, the communication device is used for wireless communication connection to a communication network.

Preferably, the communication device is a radio network node.

In another preferred embodiment, the communication device is an intermediate network node for connecting a radio network node to the communication network.

Preferably, the radiographic imaging apparatus is communicable by use of a communication network in wireless communication connection, and a storage device is connected to the communication network and stores the radiation image from the radiographic imaging apparatus.

Furthermore, an access controller is provided, and controls communication access of a radiographic imaging apparatus having an electronic cassette for forming a radiation image and wirelessly transmitting the radiation image. A storage medium stores frequency information of a frequency of a first radio communication channel used by the electronic cassette for transmitting the radiation image, and of a frequency of a second radio communication channel used by a communication device different from the radiographic imaging apparatus and communicable wirelessly. A command receiver receives a priority request signal for priority of the first radio communication channel to the electronic cassette over the communication device before the electronic cassette starts transmitting the radiation image. An overlap detector refers to the storage medium upon receiving the priority request signal, and checks presence of the communication device in which a radio communication channel of overlap of frequency on the first radio communication channel is used. A communication limiter operates in presence of the communication device with the overlap, and regulates the communication device in communication regulation while the electronic cassette transmits the radiation image.

Consequently, communication errors or delay due to radio interference of radio communication can be prevented, because overlap between radio communication channels in relation to frequency can be considered to perform communication regulation of an unnecessary radio network node.

BRIEF DESCRIPTION OF THE DRAWINGS

The above objects and advantages of the present invention will become more apparent from the following detailed description when read in connection with the accompanying drawings, in which:

FIG. 6 is a block diagram schematically illustrating a radio communication interface and a wireless access point device;

DETAILED DESCRIPTION OF THE PREFERRED EMBODIMENT(S) OF THE PRESENT INVENTION

First Preferred Embodiment

Figure 1:
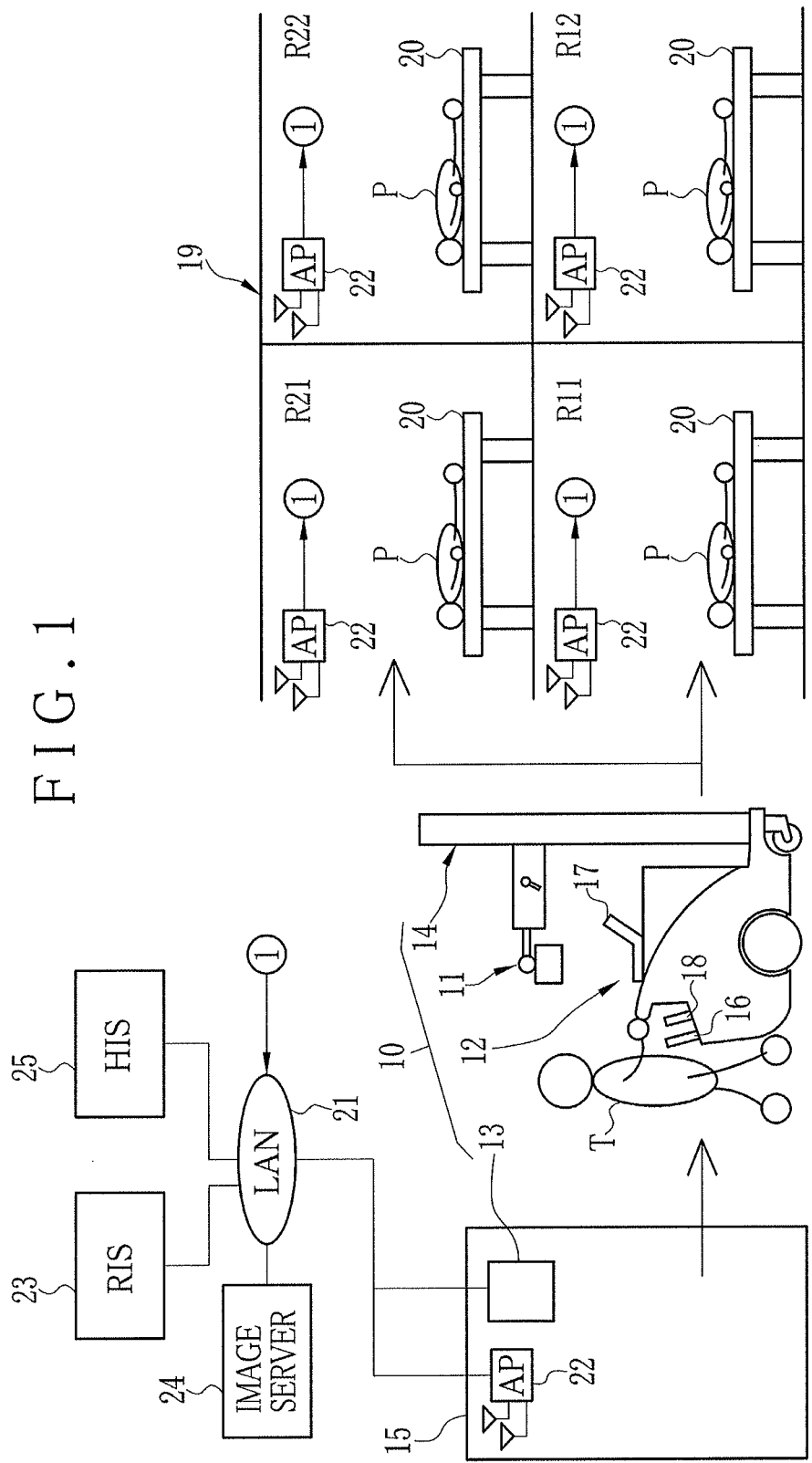
FIG. 1 is an explanatory view illustrating an X-ray imaging system with a hospital facility with the same.

In FIG. 1, an X-ray imaging system 10 as a radiographic imaging system includes an X-ray source apparatus 11 as a radiation source apparatus, an X-ray imaging apparatus 12 as a radiographic imaging apparatus, and an access controller 13 for communication access (communication environment). A medical cart 14 is constituted by the X-ray source apparatus 11 and a cart platform. The cart platform has rotatable wheels for movement, so that the X-ray source apparatus 11 is usable as a mobile radiation source apparatus. The X-ray imaging apparatus 12 includes an electronic cassette 16, a portable console unit 17 or user interface unit, and a control interface module 18 or functional unit (intermediate network node), and can be carried by the medical cart 14. There is a storage space 15 where the medical cart 14 is stored in a hospital facility 19 while the medical cart 14 is not used. For imaging in medical diagnosis, the X-ray imaging apparatus 12 is placed on the medical cart 14 which is moved out of the storage space 15. In a hospital facility 19, a technician or operator T manually moves the medical cart 14 to hospital rooms R11, R12, R21 and R22, and forms images of a body P of a patient of each of hospital beds 20.

An access point device 22 (AP) is installed in each of the hospital rooms R11, R12, R21 and R22, the storage space 15 and other places in the hospital facility 19. A local area network 21 (LAN) as a communication network is provided in the hospital facility 19. The access point device 22 is an intermediate network node for connecting a portable terminal device to the local area network 21 in the hospital facility 19. The access point device 22 (radio network node) includes a radio communication interface and a wired communication port. The radio communication interface communicates with the portable terminal device. The wired communication port operates for connection to the local area network 21 by a communication cable. The radio communication interface has an antenna, a modulator/demodulator and a transmission control device. The radio communication interface controls for transmission according to a communication protocol of the IEEE 802.11n as a typical standard of the wireless LAN available today. This is similar to radio communication interfaces 37 and 38 in the electronic cassette 16 and the portable console unit 17 of FIG. 3 to be described later. Plural systems are connected to the local area network 21, including a HIS server 25 or Hospital Information System server, a RIS server 23 or Radiology Information System server, and an image server 24.

Figure 9:
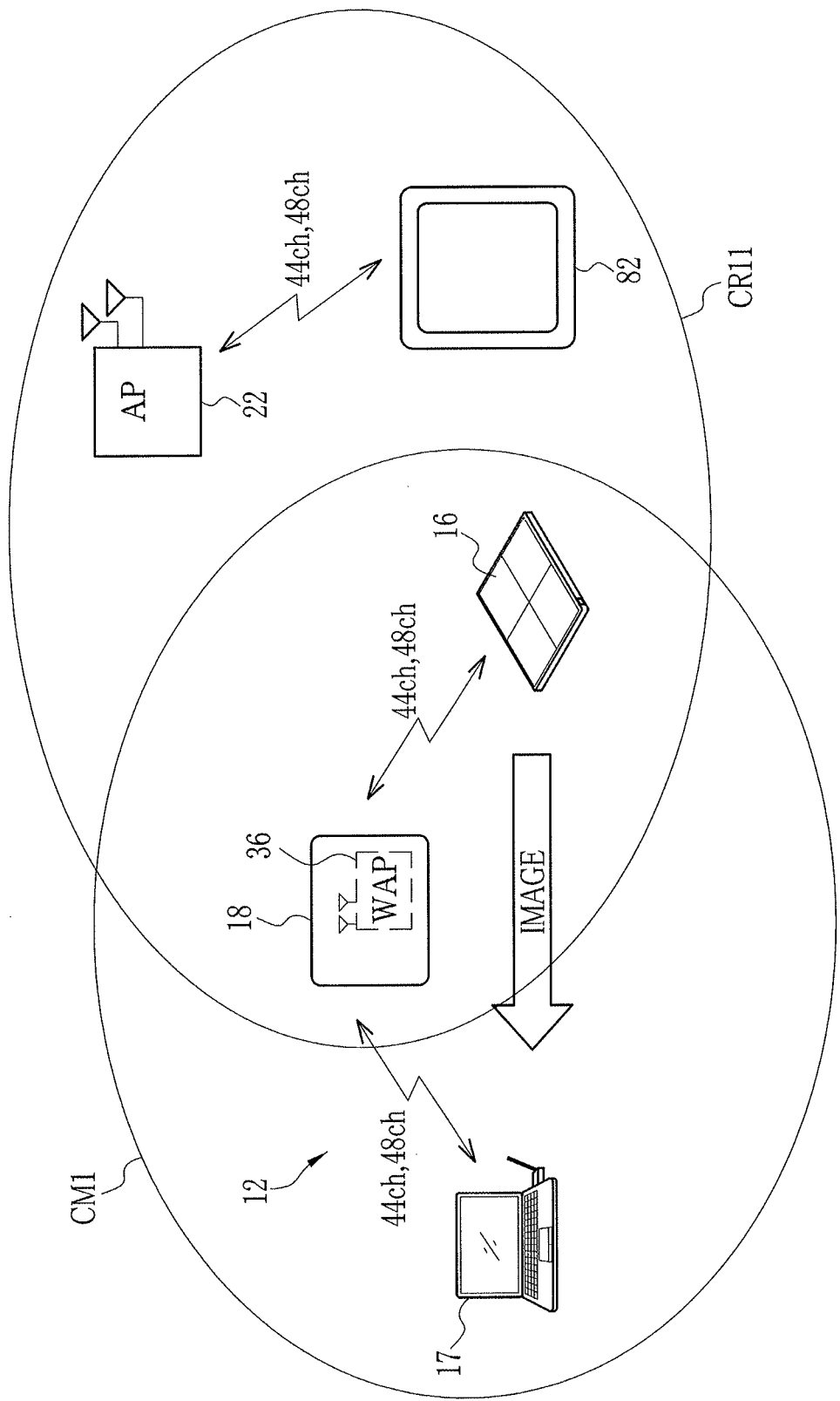
FIG. 9 is an explanatory view illustrating radio interference.

The HIS server 25 operates for managing electronic medical charts, and is mainly accessed by local terminal devices (network nodes) which doctors, nurses and the like use in hospital departments, such as internal medicine, surgery and the like. Examples of the local terminal devices include a desktop computer, notebook computer, tablet computer (a portable terminal device 82 of radio communication of FIG. 9), and the like. The local terminal devices are used to view the medical charts, input information of diagnosis or treatment and the like.

The RIS server 23 is established by a radiology department, and used for managing imaging requests as request information from hospital departments to the radiology department. Information of the imaging request includes requester information, case information, body part information, direction information, and note information. Requesters of the requester information include a hospital department and a name of a doctor (physician). Examples of the case information include a name, age and sex of a patient (body). Body parts of the body part information include a head, chest, abdomen, hands, fingers and the like. Imaging directions of the direction information include a front direction, lateral direction, diagonal direction, PA (posteroanterior direction) and AP (anteroposterior direction). Examples of the note information include a purpose of imaging, progress note and message from the doctor (physician). The operator T checks the imaging request with the portable console unit 17, determines an imaging condition suitable for the imaging request, and sets the imaging condition in the electronic cassette 16 and the X-ray source apparatus 11.

The imaging condition includes an irradiation condition, which is defined by a tube voltage (kV), a tube current (mA) and irradiation time (sec) of X-rays. The tube voltage determines energy spectrum of X-rays from the X-ray source apparatus 11. The tube current determines a radiation dose per unit time. A cumulative radiation dose of X-rays is determined as a product of multiplication of the tube current and irradiation time. Input data of the irradiation condition can be values of the tube current and irradiation time, and can be a value of a current-time product (mAs) of the tube current and irradiation time.

The image server 24 stores and manages image data of X-ray images formed by the X-ray imaging apparatus 12 according to an imaging request. Access to the image server 24 is possible even from a local terminal device disposed at a requester of the imaging request. A physician or operator with the terminal device can view X-ray images by accessing the image server 24.

Figure 3:
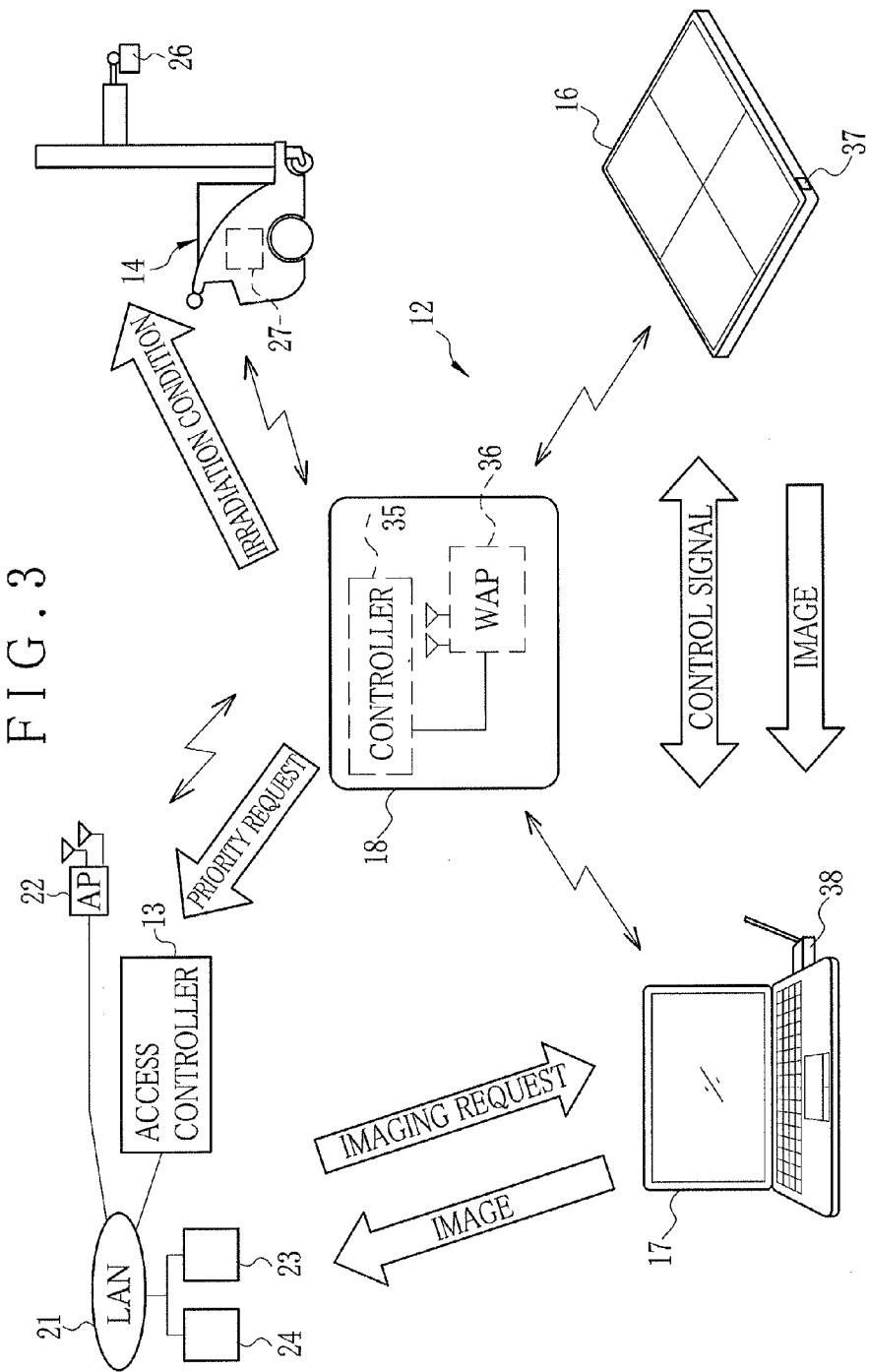
FIG. 3 is a block diagram schematically illustrating an X-ray imaging apparatus.

In the X-ray imaging apparatus 12, the portable console unit 17 is a radio network node (wireless terminal device) of radio communication. A wireless access point device 36 (WAP) of FIG. 3 is incorporated in the control interface module 18, and makes the portable console unit 17 communicable with the electronic cassette 16. Also, the portable console unit 17 becomes connected to the local area network 21 by the wireless access point device 36 and the access point device 22, and accesses to the RIS server 23 and the image server 24. The portable console unit 17 receives and acquires an imaging request from the RIS server 23, and transmits X-ray images to the image server 24. The imaging request is downloaded to the portable console unit 17 through the access point device 22 located in the storage space 15 before starting the imaging in the in-patient care. The X-ray images are uploaded to the image server 24 through each of the access point devices 22 located in the hospital facility 19 or the storage space 15.

The access controller 13 controls the communication environment of the X-ray imaging apparatus 12. This is for the purpose of preventing radio interference between the X-ray imaging apparatus 12 and the access point device 22 or other portable terminal devices connected to the access point device 22 (in short, radio network nodes), in the course of wireless transmission of an X-ray image from the electronic cassette 16 to the portable console unit 17, which will be described later. The access controller 13 is connected to the local area network 21 by a communication cable. The access controller 13 transmits a command signal of control to each of the access point devices 22 in the hospital facility 19 for the in-patient care by use of the local area network 21. The access controller 13 is disposed, for example, in the storage space 15. Even while the medical cart 14 with the X-ray imaging apparatus 12 is located in the hospital facility 19, the access controller 13 is communicable with the X-ray imaging apparatus 12 through one of the access point devices 22 in the hospital facility 19 and the local area network 21.

Figure 2:
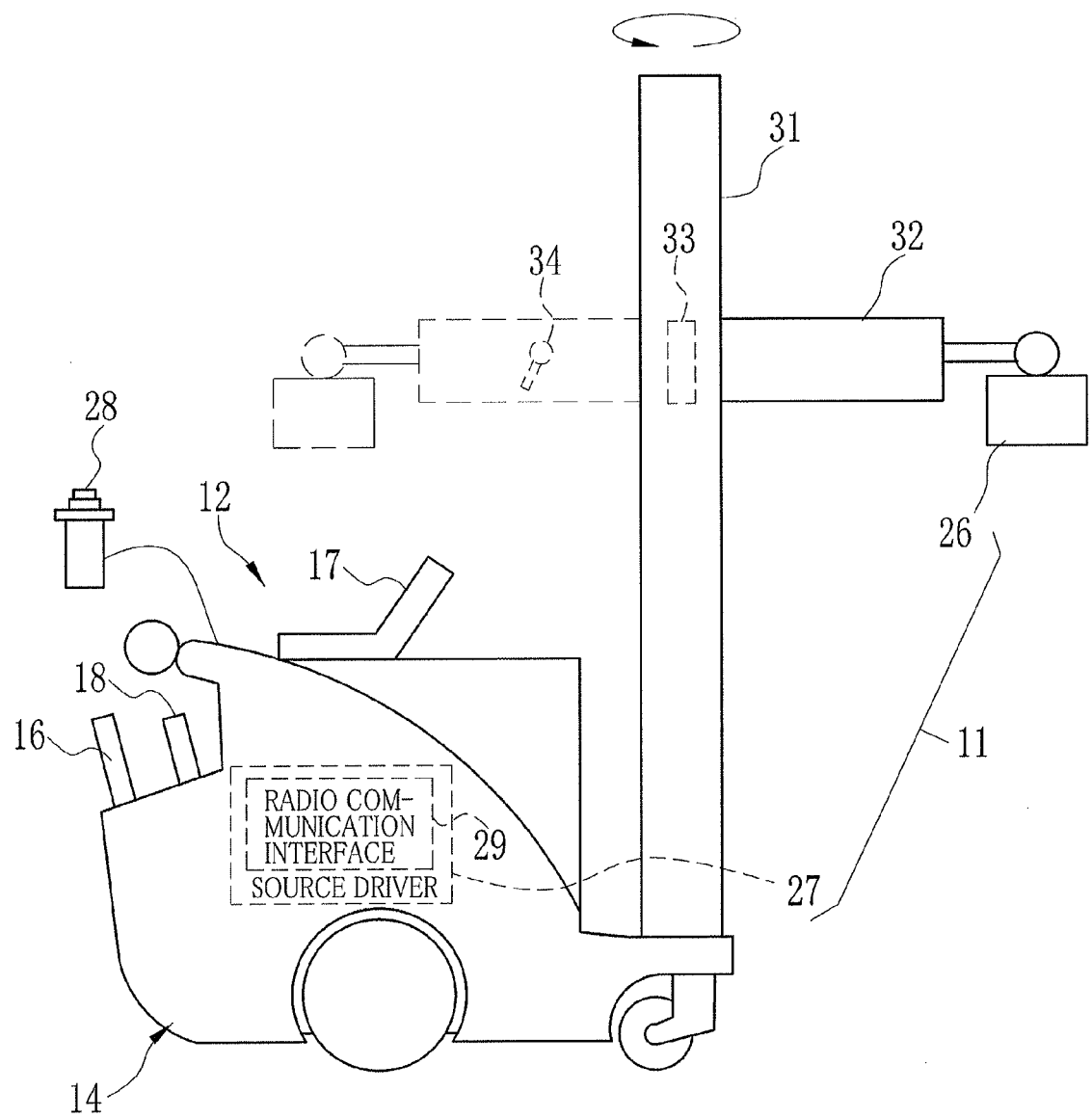
FIG. 2 is a side elevation illustrating a medical cart.

In FIG. 2, the X-ray source apparatus 11 includes an X-ray source 26 as a radiation source, a source driver 27 (controllable) and a start switch 28. The source driver 27 controls the X-ray source 26. The X-ray source 26 includes an X-ray tube (not shown) and a collimator (not shown). The X-ray tube emits X-rays. The collimator limits a path of irradiation to an object downstream of the X-ray tube. Various elements are associated with the X-ray tube, including a filament (cathode) and target (anode). The filament generates thermal electron. The target emits X-rays by collision of the thermal electron from the filament. The collimator is constituted by four movable plates of metal lead arranged quadrilaterally for blocking X-rays. An emission opening of a quadrilateral shape is defined in the collimator at the center for transmitting X-rays.

A support column 31 is disposed in the medical cart 14 to extend vertically. A support arm 32 is disposed on the support column 31 to extend horizontally. The X-ray source 26 is supported at a distal end of the support arm 32. The support column 31 is rotatable about its longitudinal axis. The support arm 32 and the X-ray source 26 are rotated by rotation of the support column 31. The support arm 32 is movable up and down relative to the support column 31. The X-ray source 26 is supported on the support arm 32 in a rotatable manner. Thus, a position of irradiation and direction of the X-ray source 26 are adjusted by rotation of the support column 31, vertical movement and extension of the support arm 32, and rotation of the X-ray source 26. A lock mechanism 33 is disposed in the support column 31. The lock mechanism 33 is operated while the medical cart 14 is run and prevents the support column 31, the support arm 32 and the X-ray source 26 from shifting incidentally. For example, the lock mechanism 33 includes a lock pin movable between a first position for regulating the shift of the X-ray source 26 and a second position for allowing the X-ray source 26 to shift by release. In case a lock button 34 is depressed, the lock pin is moved to engage and release the lock mechanism 33.

The source driver 27 includes a high voltage source and a controller. The high voltage source supplies the X-ray source 26 with high voltage. The controller controls the tube voltage, tube current and irradiation time. The high voltage source includes a transformer and a high voltage cable. The transformer boosts an input voltage to generate the high voltage or tube voltage. The high voltage cable supplies the X-ray source 26 with the tube voltage or drive voltage. An input panel (not shown) of the source driver 27 is manually operated by the operator T, and inputs an irradiation condition including the tube voltage, tube current and irradiation time. Also, an irradiation condition can be transmitted by the portable console unit 17 to the source driver 27 and input in the source driver 27.

The start switch 28 is operated by the operator T, and connected to the source driver 27 by a signal cable. The start switch 28 is a button of a two-step type. The start switch 28, upon being depressed halfway at a first step, generates a warmup signal for warming up the X-ray source 26, and upon being depressed fully at a second step, generates a start signal for irradiation of the X-ray source 26. Those signals are input by the signal cable to the source driver 27.

The source driver 27 controls operation of the X-ray source 26 according to a start signal from the start switch 28. Upon inputting the start signal, the source driver 27 starts powering the X-ray source 26. A timer is started and measures elapsed time upon the start of irradiating X-rays. In case the elapsed time becomes equal to the predetermined irradiation time in the irradiation condition, the source driver 27 stops irradiation of X-rays. The irradiation time changes according to the irradiation condition. Also, the source driver 27 operates assuming that the measured time becomes equal to a maximum irradiation time predetermined in the source driver 27 for the fail-safe purpose. The actual irradiation time according to the irradiation condition is determined in a range of the maximum irradiation time.

A radio communication interface 29 is incorporated in the source driver 27, and includes antenna, a modulator/demodulator and a transmission control device in a manner similar to the radio communication interface 37 in the electronic cassette 16 of FIG. 6.

In FIG. 3, the control interface module 18 of the X-ray imaging apparatus 12 includes a controller 35 and the wireless access point device 36. The controller 35 controls various circuit elements in the control interface module 18. The wireless access point device 36 communicates wirelessly between the electronic cassette 16 and the console unit 17. The electronic cassette 16 communicates with the console unit 17 in an infrastructure mode with the wireless access point device 36 instead of an ad-hoc mode for direct communication. Also, there is a client mode in the wireless access point device 36 to function as an intermediate network node in relation to the access point device 22, so that the wireless access point device 36 communicates wirelessly with the access point device 22 to connect the console unit 17 to the local area network 21 through the access point device 22.

The controller 35 outputs a priority request signal to the access controller 13. The priority request signal expresses priority to the X-ray imaging apparatus 12 for use over other radio network nodes (including a portable terminal device and the access point devices 22) in relation to a radio communication channel for radio waves used by the X-ray imaging apparatus 12. The access controller 13 in response to the priority request signal regulates the communication for the other radio network nodes, to control the communication environment of the X-ray imaging apparatus 12. Thus, the X-ray imaging apparatus 12 is designated with the priority for transmitting X-ray images from the electronic cassette 16 to the console unit 17. The priority request signal is transmitted to the access controller 13 through the wireless access point device 36, the access point device 22 and the local area network 21.

A time point of issuing a priority request signal is a time point of detecting start of irradiation of the electronic cassette 16, which will be described later. The electronic cassette 16 has a function of detecting a start of irradiation of X-rays, and sends a start flag to the console unit 17 upon detecting the start. The controller 35 receives the start flag through the wireless access point device 36, and recognizes the detection of the start of the irradiation from the electronic cassette 16. Upon terminating the reception of an X-ray image, the controller 35 transmits an end flag to the access controller 13. The access controller 13 terminates the communication regulation (access regulation) in response to the end flag.

The radio communication interfaces 37 and 38 are incorporated in the electronic cassette 16 and the console unit 17 according to the wireless LAN standard of the IEEE 802.11n similar to the radio communication interface 29. The electronic cassette 16 communicates with the console unit 17 by wireless communication connection of the radio communication interfaces 37 and 38 to the wireless access point device 36. The console unit 17 transmits signals to the electronic cassette 16, the signals including an imaging condition and a control signal, such as an enable signal (standby signal) input by an technician or operator T. In turn, the electronic cassette 16 transmits signals to the console unit 17, the signals including a response to the control signal, and an X-ray image detected by the electronic cassette 16.

The electronic cassette 16 upon receiving the enable signal is set in a ready state (enabled state) for imaging.

The console unit 17 is connected to the local area network 21 by the wireless access point device 36, so as to access the RIS server 23 and the image server 24. The console unit 17 can download an imaging request from the RIS server 23, and can upload an X-ray image to the image server 24. Also, the wireless access point device 36 transmits (or relays) the radio communication between the console unit 17 and the source driver 27 carried by the medical cart 14. Thus, an irradiation condition can be wirelessly transmitted from the console unit 17 to the source driver 27. Transmission of the irradiation condition from the console unit 17 makes it unnecessary manually to input the irradiation condition to the source driver 27 by use of a user input interface in the medical cart 14. Also, the X-ray imaging apparatus 12 is enabled by the wireless access point device 36 to receive a turn-on signal of the start switch 28 from the source driver 27.

Figure 4:
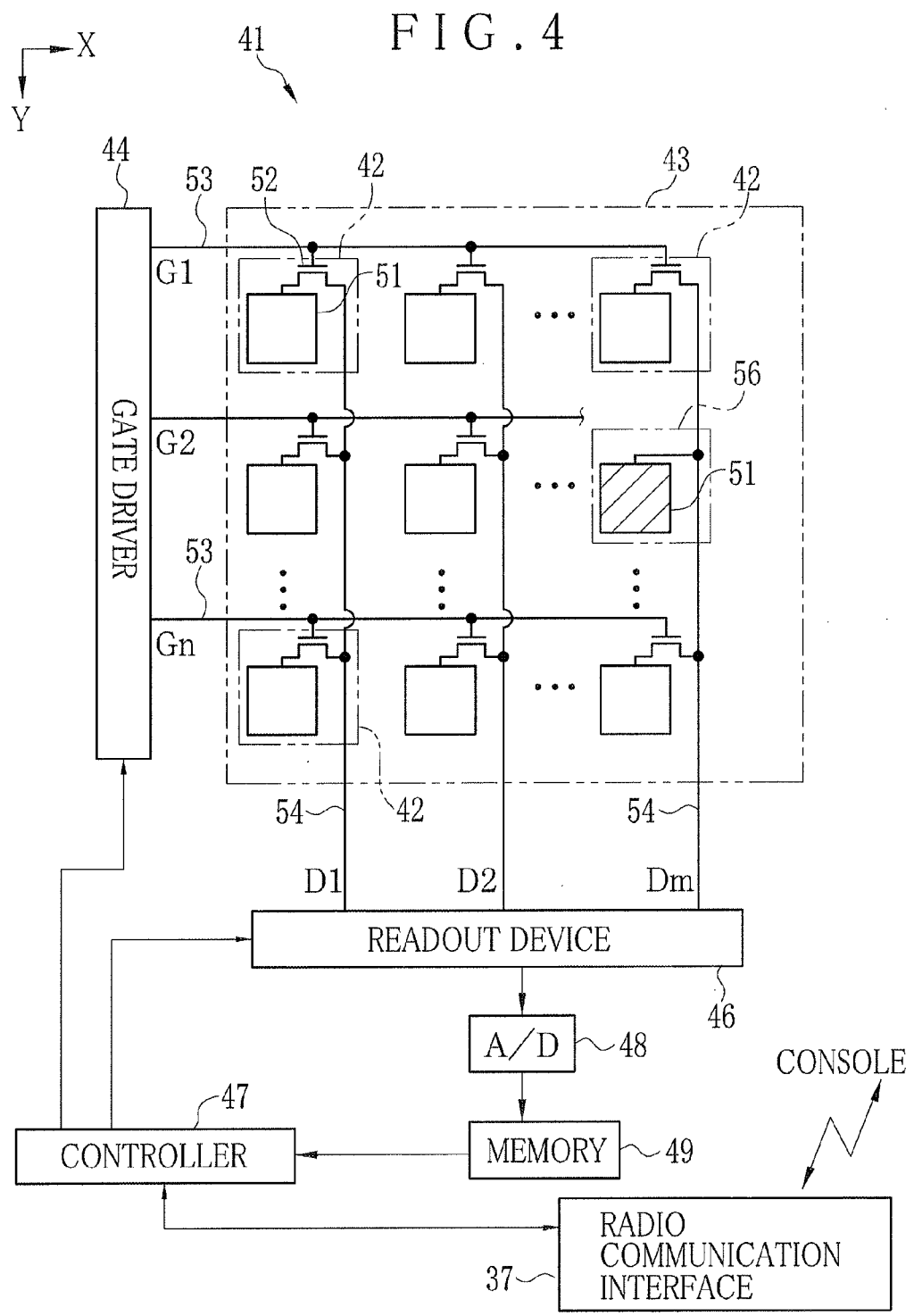
FIG. 4 is a block diagram schematically illustrating a sensor panel.

The electronic cassette 16 is constituted by a sensor panel 41 or flat panel detector (FPD) of FIG. 4, and a portable housing for containing the sensor panel 41. The electronic cassette 16 is a portable X-ray imaging apparatus for receiving X-rays passed through the body P irradiated by the X-ray source 26, and detecting an X-ray image of the body P. The portable housing is formed in a flat plate shape in a size approximately equal to that of a film cassette and IP cassette.

In FIG. 4, the sensor panel 41 includes a TFT active matrix substrate, a gate driver 44, a readout device 46, a controller 47, an A/D converter 48, a memory 49 and the radio communication interface 37. An active pixel area 43 is disposed on the active matrix substrate. A battery (not shown) is contained in the housing for driving various elements in the sensor panel 41.

Pixels 42 are arranged in the active pixel area 43 for storing signal charge according to an incident radiation dose of X-rays, and in a matrix form of n rows and m columns in X and Y-directions. The numbers n and m are integers equal to or more than 2, for example, both approximately 2,000. Note that the arrangement of the pixels 42 can be a honeycomb arrangement instead of the rectangular arrangement of the present embodiment. The sensor panel 41 is constituted by a scintillator (not shown) for converting X-rays into visible light. The sensor panel 41 is an indirect conversion type in which visible light from the scintillator is converted photoelectrically by the pixels 42. The scintillator includes phosphor, such as thallium activated cesium iodide (CsI:Tl), and GOS or terbium activated gadolinium oxysulfide ($Gd_2O_2S$:Tb), and is opposed to the entire surface of the active pixel area 43 with the pixels 42. Note that the sensor panel 41 can be a direct conversion type for directly converting X-rays into signal charge, instead of the indirect conversion type.

Each of the pixels 42 includes a photo diode 51 and a thin film transistor 52 (TFT). The photo diode 51 generates charge (electron/hole pair) upon entry of visible light and stores the charge. The thin film transistor 52 is a switching element. The photo diode 51 includes a semiconductor layer of a-Si (amorphous silicon), and upper and lower electrodes between which the semiconductor layer is disposed. The semiconductor layer is a PIN type (p-intrinsic-n type). The lower electrode of the photo diode 51 is connected with the thin film transistor 52. To the upper electrode, bias voltage is applied. An electric field is created in the semiconductor layer by application of the bias voltage. An electron-hole pair is created in the semiconductor layer by the photoelectric conversion. An electron moves to the upper electrode with a positive polarity. The positive hole moves to the lower electrode with a negative polarity, so that the photo diode 51 stores charge by way of a capacitor.

In the thin film transistor 52, a gate electrode is connected to scan lines 53. A source electrode is connected to signal lines 54. A drain electrode is connected to the lower electrode of the photo diode 51. The scan lines 53 and the signal lines 54 are arranged transversely in a quadrilateral form. The number of the scan lines 53 is n or the number of rows of the pixels 42 in the active pixel area 43. The number of the signal lines 54 is m or the number of columns of the pixels 42. The scan lines 53 are connected to the gate driver 44. The signal lines 54 are connected to the readout device 46.

The gate driver 44 drives the thin film transistor 52 while controlled by the controller 47, and causes the sensor panel 41 to operate in functions of the storing, readout and reset. In the storing, signal change according to an incident radiation dose of X-rays is stored in the pixels 42. In the readout, the signal charge in the pixels 42 is readout. In the reset, unwanted charge in the pixels 42 is eliminated. While X-rays are applied, the gate driver 44 turns off the thin film transistor 52 of all the pixels 42, to start the pixels 42 storing the signal charge. After irradiation of the X-rays, gate pulses G1-Gn are input sequentially to the scan lines 53, to turn on the thin film transistor 52 by one pixel row, for reading out the signal charge. The signal charge from the pixels 42 is read out on the signal lines 54, and input to the readout device 46.

The photo diode 51 generates dark current charge irrespective of incidence of X-rays. The dark current charge is a noise component in relation to image data. To remove the dark current charge, reset of pixels is performed before irradiation of X-rays. The reset is operation of sweeping dark current charge at the pixels 42 through the signal lines 54.

The readout device 46 reads the signal charge D1-Dm from the pixels 42. The controller 47 controls various elements in the readout device 46. The A/D converter 48 converts the signal charge into digital data, which is written to the memory 49.

The readout device 46 includes integrating amplifiers and a multiplexer. Each of the integrating amplifiers converts the signal charge read out from the pixels 42 into a voltage signal. The multiplexer sequentially changes over columns of the pixels 42 in the active pixel area, and outputs a voltage signal per one column. In the readout operation, the voltage signal input to the readout device 46 is converted by the A/D converter 48 into digital data, which is written to the memory 49 as digital image data. Also, the image data read from the memory 49 is transmitted by the radio communication interface 37 to the console unit 17.

In the reset, the thin film transistors 52 of the pixels 42 are sequentially turned on by the unit of a pixel row, to input the dark current charge from the pixels 42 to the readout device 46, in a manner similar to the readout. However, the dark current charge in the reset is abandoned by resetting the integrating amplifiers, and is not output to the A/D converter 48. The reset is started upon powering of the electronic cassette 16, and repeated at a predetermined interval of time. In case the electronic cassette 16 becomes in the ready state for imaging, the reset is interrupted. Shortly before the start of storing in the pixels 42, the reset of one frame is performed for one time.

Also, detection sensors 56 are disposed in the active pixel area 43 in a form included in part of the group of the pixels 42. The detection sensors 56 operate for detecting a start of irradiation of X-rays. The detection sensors 56 have the photo diode 51 similarly to the pixels 42, but do not have the thin film transistor 52. The photo diode 51 and the signal lines 54 are short-circuited. An output of the detection sensors 56 (charge generated by the photo diode 51) is caused to flow to the signal lines 54 irrespective of turn-on or turn-off of the thin film transistor 52 in the pixels 42.

The output of the detection sensors 56 is read out to the memory 49 by the readout device 46 and the A/D converter 48 in a manner similar to the pixels 42. The readout of the detection sensors 56 is performed at such a short period as μsec. An output of the detection sensors 56 obtained by the readout of one event is an incident radiation dose of X-rays per unit time. Upon start of irradiation, the incident radiation dose per unit time gradually increases, to increase the output of the detection sensors 56.

The controller 47 reads out the output at each time that the output of the detection sensors 56 is stored to the memory 49. The controller 47 compares the output of the detection sensors 56 with a predetermined threshold for the start, and judges a start of the irradiation of X-rays in response to becoming of the output as high as the threshold. Thus, the sensor panel 41 can function for detecting the start of irradiation without receiving a sync signal from the X-ray source apparatus 11. Also, the output of the detection sensors 56 can be read out even while the sensor panel 41 operates for the storing, so that the controller 47 can also detect termination of irradiation of X-rays by considering the output of the detection sensors 56.

After the power supply for the electronic cassette 16 is turned on, the sensor panel 41 starts the reset of the pixels 42. In case the enable signal from the console unit 17 is received, the sensor panel 41 terminates the reset, and becomes in the ready state. The sensor panel 41 starts detection of irradiation, namely starts readout of an output of the detection sensors 56. Upon detecting the start of irradiation of X-rays, the sensor panel 41 performs the reset of one frame, and turns off the thin film transistor 52 of the pixels 42 to start the storing. In case the start of irradiation is detected, the sensor panel 41 transmits a start flag to the console unit 17 through the radio communication interface 37. The sensor panel 41 continues the readout of the detection sensors 56 even after starting the storing. In case the output of the readout becomes equal to or lower than a threshold of the termination, the controller 47 detects the termination of irradiation. In response to this, the sensor panel 41 terminates the storing, and starts the readout of an X-ray image.

In FIG. 3, the console unit 17 includes a notebook computer and a application program installed therein. The notebook computer has a computer main unit and a display device associated with the computer main unit. The computer main unit includes a CPU (central processing unit) and a storage medium, such as a memory and a hard disk drive.

Figure 5:
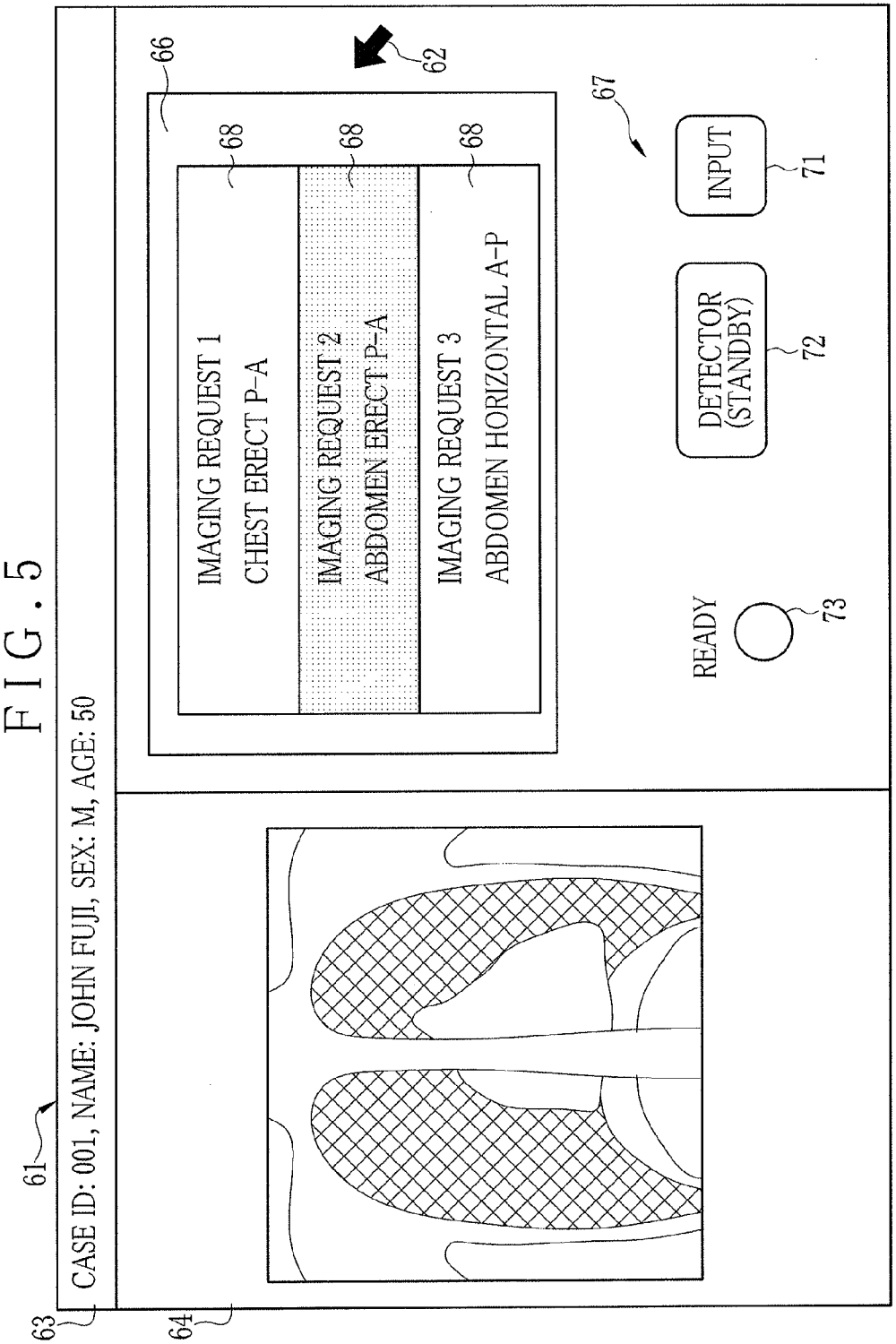
FIG. 5 is an explanatory view in a plan illustrating a screen in a console unit.

In FIG. 5, an input screen 61 of the GUI (graphical user interface) appears on the display device of the console unit 17 upon running the application program. A pointer 62 is displayed in the input screen 61 for pointing a partial area. An input device is connected to the console unit 17, for manipulating the pointer 62, such as a mouse, trackpad and the like.

The input screen 61 includes an information area 63, an image area 64, a request area 66 and a button area 67. An imaging request 68 received from the RIS server 23 is disposed in the request area 66. In case one of the imaging requests 68 is selected by use of the pointer 62, the imaging request 68 is indicated by a change in the color distinctly from those unselected in the imaging requests 68. Case information of the body is displayed in the information area 63 in connection with the imaging request 68, such as a name, case ID, age and sex of a patient (body).

The image area 64 is for displaying an X-ray image transmitted by the electronic cassette 16 after imaging. In FIG. 5, the X-ray image appears in the image area 64. However, no image appears in the image area 64 before the imaging. It is possible with the image area 64 to check the X-ray image immediately after the imaging. The operator T views the X-ray image in the image area 64, and checks propriety in the imaging. In case the imaging request 68 is selected in the request area 66, an X-ray image corresponding to the imaging request 68 is displayed in the image area 64.

The button area 67 includes an input button 71, a detector button 72 (standby button) and an indicator 73. The input button 71 is operable for inputting an imaging condition and various conditions for the electronic cassette 16. In case the pointer 62 points the input button 71, a setting screen is caused to appear. The detector button 72 is operable for transmitting an enable signal to the electronic cassette 16. The console unit 17 transmits the enable signal to the electronic cassette 16 upon operating the detector button 72. In response to this, the electronic cassette 16 performs a task for the ready state (enabled state), and then transmits a ready flag to the console unit 17 upon completion of the task for the ready state. The indicator 73 is turned on upon receiving the ready flag at the console unit 17. The operator T can visually check the electronic cassette 16 in the standby state by use of the indicator 73.

In FIG. 6, the radio communication interface 37 in the electronic cassette 16 includes an antenna 75, a modulator/demodulator 76 and a transmission control device 77. The modulator/demodulator 76 combines a carrier wave with data to be transmitted by performing modulation, and also acquires data from the carrier wave received through the antenna 75 by performing demodulation.

The transmission control device 77 controls transmission according to a wireless LAN standard. Examples of communication protocols are TCP/IP (Transmission Control Protocol/Internet Protocol) and the IEEE 802.11n. The communication protocols are provided in layers according to the model of reference of the OSI (Open Systems Interconnection). The plural communication protocols of different layers are combined together for use. The TCP/IP is used even in the wired LAN, and is a communication protocol of an upper layer in the wireless LAN standard. The IEEE 802.11n is a communication protocol of a layer lower than the TCP/IP, and determines steps of communication particular to the radio communication. It is possible in the IEEE 802.11n to use radio waves of a band of 2.4 GHz or 5 GHz for radio communication channels. The X-ray imaging system 10 of the electronic cassette 16 of the present embodiment uses the band of 5 GHz.

Also, the wireless access point device 36 in the control interface module 18 has an antenna 78, a modulator/demodulator 79 and a transmission control device 80. The transmission control device 80 operates for radio communication according to the IEEE 802.11n similar to the transmission control device 77 in the electronic cassette 16. Note that the radio communication interface 38 in the console unit 17, the radio communication interface 29 in the source driver 27 and the access point device 22 are communicable in the radio communication according to the IEEE 802.11n.

As described above, the wireless access point device 36 in the X-ray imaging apparatus 12 communicates wirelessly between the electronic cassette 16 and the console unit 17 by wireless communication connection. No cable for wired connection is used in the wireless communication connection. Logical communication link must be established between the wireless access point device 36 and each of the electronic cassette 16 and the console unit 17. The wireless access point device 36 operates as a host in the wireless communication connection. The electronic cassette 16 and the console unit 17 operate as radio communication terminals in connection with the wireless access point device 36. The following is methods and steps of connection and communication defined according to the IEEE 802.11n with the electronic cassette 16 and the wireless access point device 36.

Figure 7:
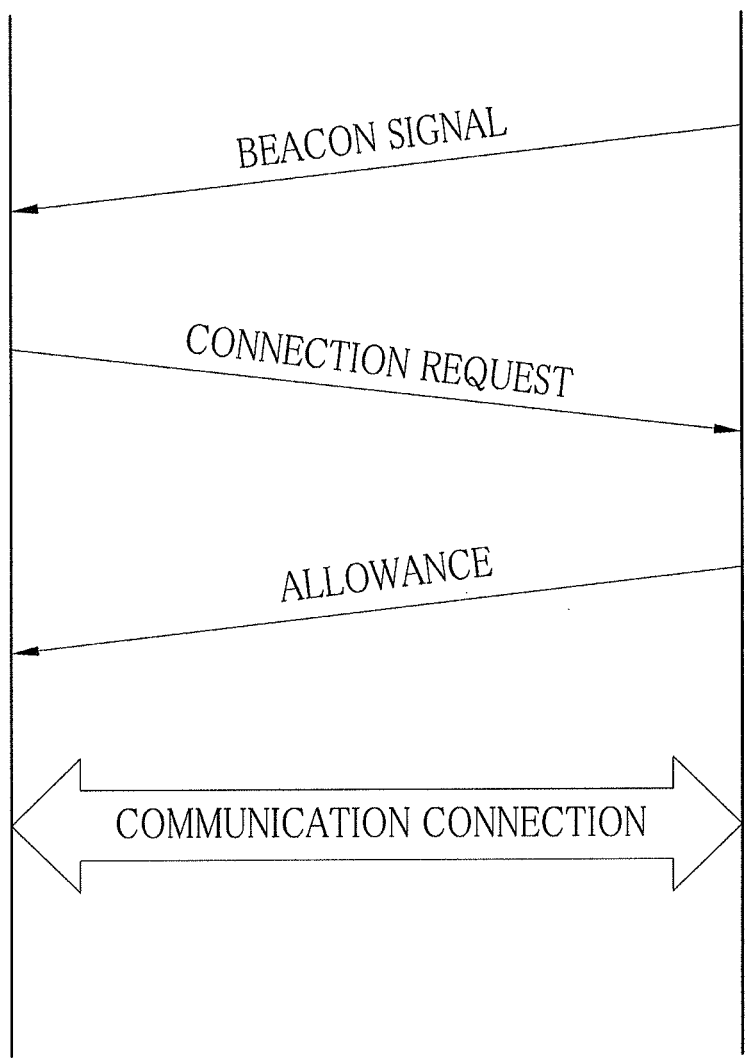
FIG. 7 is a timing chart illustrating a connection sequence to the wireless access point device.

In a connection sequence of the wireless communication connection between the electronic cassette 16 and the wireless access point device 36 of FIG. 7, at first the wireless access point device 36 transmits a beacon signal or radio waves at a predetermined interval as long as 100 msec. The beacon signal is for the purpose of notifying the electronic cassette 16 and the like of the presence of the wireless access point device 36 at a small distance. The radio communication interface 37 in the electronic cassette 16 in an active state constantly monitors occurrence of the beacon signal. The radio communication interface 37 is ready to receive the beacon signal while located in a range of reach of the beacon signal from the wireless access point device 36.

A network identifier is included in the beacon signal, for example, SSID (Service Set Identifier) and ESSID (Extended Service Set Identifier). The network identifier is information for identifying the access points and the network having the access points from the electronic cassette 16 as radio network node, examples of the access points including the wireless access point device 36 and the access point device 22.

In the electronic cassette 16, a network identifier predetermined for the wireless access point device 36 is stored in the radio communication interface 37 to block connection to a foreign access point other than the wireless access point device 36 in the control interface module 18. The radio communication interface 37 receives a beacon signal with the network identifier set for the wireless access point device 36, and then transmits a connection request to the wireless access point device 36. Radio network nodes allowable to the wireless access point device 36 for connection are limited to the electronic cassette 16 and the console unit 17. The wireless access point device 36 performs authorization for a requester or radio network node with the connection request. Thus, the electronic cassette 16 transmits information and the connection request to the wireless access point device 36 inclusive of authorization information, password and the like.

The wireless access point device 36 in response to the connection request performs authorization by verifying the received password with a predetermined password, and transmits a response of allowance to the electronic cassette 16 in the case of coincidence of the password. The response of allowance includes an IP address (Internet Protocol address) for assignment to the electronic cassette 16. A logical communication link is established by receiving the response in the electronic cassette 16, to connect the electronic cassette 16 with the wireless access point device 36 in the wireless communication connection.

Also, connection is established between the wireless access point device 36 and the console unit 17 in a similar manner to that between the wireless access point device 36 and the electronic cassette 16. The wireless access point device 36 assigns IP addresses to the electronic cassette 16 and the console unit 17. Data communication is enabled between the electronic cassette 16 and the console unit 17 owing to the intermediate function of the wireless access point device 36. The communication with the IP addresses is performed according to the TCP/IP.

The connection sequence as described heretofore is repeated also for wireless communication connection between a portable terminal device and the access point device 22, and for connection between the wireless access point device 36 and the access point device 22 during setting of the wireless access point device 36 in the client mode. To all of the access point devices 22 disposed in the hospital facility 19, network identifiers and passwords are predetermined for connection to the wireless access point device 36 and a portable terminal device.

Even after becoming connected with the electronic cassette 16, the wireless access point device 36 continues transmitting the beacon signal. The connection between the electronic cassette 16 and the wireless access point device 36 is continued while the electronic cassette 16 receives the beacon signal, and is terminated upon termination of receiving the beacon signal at the electronic cassette 16. Examples of the termination include a stop of transmitting the beacon signal from the wireless access point device 36, and a change in the location of the electronic cassette 16 to the outside of a reception area of the beacon signal from the wireless access point device 36. In case the electronic cassette 16 is entered again in the reception area of the beacon signal and enabled to receive the same, then the connection is made again.

A frequency of one radio communication channel is assigned to each one of the access point devices including the wireless access point device 36 and the access point device 22. A beacon signal is transmitted at the frequency assigned to the access point device. The electronic cassette 16 determines a frequency of generated radio waves according to frequency of the beacon signal. Thus, the frequency of the radio communication channel used between the electronic cassette 16 and the wireless access point device 36 is determined. In the IEEE 802.11n, radio waves of bands of 2.4 GHz and 5 GHz are used. Those are divided in plural radio communication channels for use.

Figure 8:
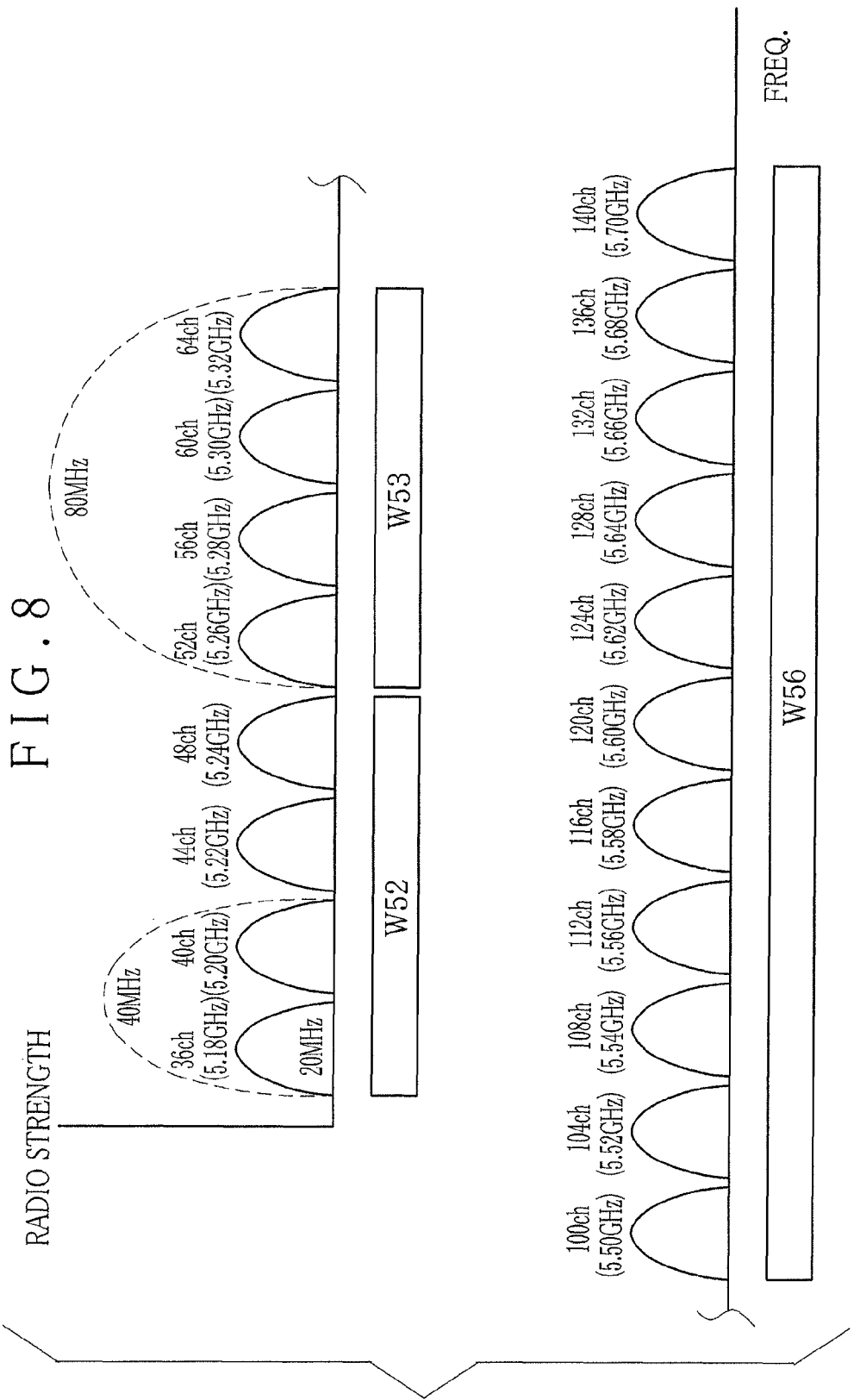
FIG. 8 is a graph illustrating frequencies of radio communication channels.

In FIG. 8, the frequency band of 5 GHz is from 5.15 GHz to 5.725 GHz. This band is divided into frequency sub-bands of 5.2 GHz (W52), 5.3 GHz (W53) and 5.6 GHz (W56). Also, each of the frequency sub-bands has plural radio communication channels each of which has a width of 20 MHz.

The frequency sub-band W52 is divided into four channels, namely 36th, 40th, 44th and 48th channels. Center frequencies of those four channels are 5.18, 5.20, 5.22 and 5.24 GHz. The frequency sub-band W53 is divided into four channels, namely from 52nd channel (center frequency of 5.26 GHz) to 64th channel (center frequency of 5.32 GHz). The frequency sub-band W56 is divided into 11 channels, namely from 100th channel (center frequency of 5.50 GHz) to 140th channel (center frequency of 5.70 GHz). Accordingly, it is possible to use 19 radio communication channels in the entirety of the frequency band of 5 GHz, as each one channel has a width of 20 MHz.

In the band of 5 GHz, it is theoretically possible to assign radio communication channels without frequency overlap in a range of 19 or less access point devices. The access point devices can be free from radio interference owing to this assignment. However, frequency overlap occurs in a range of more than 19 access point devices, because a radio communication channel of an equal frequency is used by two or more access point devices.

In the IEEE 802.11n, two channels of a width of 20 MHz are combined together to form one channel with a larger width of 40 MHz, as indicated by the broken line in the frequency sub-band W52. This technique is referred to as channel bonding. The larger width of each one channel owing to the channel bonding enables communication of a high speed. Two channels with the width of 20 MHz are assigned to one access point device by fully using the channel bonding for all of the access point devices.

For this use, the number of radio communication channels available for simultaneous use free from radio interference in the band of 5 GHz is 9 channels. Accordingly, frequency overlap occurs in a range of more than 9 access point devices, because a radio communication channel of an equal frequency is used by two or more access point devices.

For example, frequencies of channels used by the wireless access point device 36 in the X-ray imaging apparatus 12 overlap on frequencies of channels used by the access point device 22 in the hospital room R11, such as 44th and 48th channels. See FIG. 9. Assuming that a communication cell CM1 as a range of reach of radio waves of the wireless access point device 36 overlaps on a communication cell CR11 as a range of reach of radio waves of the access point device 22, then radio interference occurs between the electronic cassette 16 and a portable terminal device 82 of radio communication (radio network node) for connection to the access point device 22, to create a communication error or delay. The portable terminal device 82 is manually used by a physician, nurse or the like in hospital departments.

In the IEEE 802.11ac as a succeeding standard to the IEEE 802.11n, channel bonding of four channels is possible owing to the innovation of the technology in the channel bonding, as indicated by the broken line in the frequency sub-band of W53 in FIG. 8. A width of each one channel is 80 MHz with the channel bonding of four channels, the transmission speed can be still higher. In contrast, the number of the channels for simultaneous use free from radio interference in the band of 5 GHz is as small as four. The overlap between frequencies is increased between access point devices.

In compliance with legal requirement of a country, region or the like with local regulation, it is likely that use of partial channels is restricted publicly. For example, use of frequency sub-bands of W53 and W56 is inhibited in Japan in an outdoor environment, because of their frequency overlap on a radar system. It is likely that only the frequency sub-band W52 is used without using the frequency sub-bands W53 and W56 even in the indoor environment for the use of the band of 5 GHz in Japan. In short, the number of the available channels becomes lower. In the band of 2.4 GHz, the number of available channels for simultaneous use without radio interference is as small as three with a width of 22 MHz, which is a smaller number than that in the band of 5 GHz. In consideration of those situations, it is necessary to consider prevention of frequency overlap or radio interference.

In the standard of the IEEE 802.11n, a method of CSMA/CA (carrier sense multiple access/collision avoidance) is used for preventing radio interference.

Figure 10:
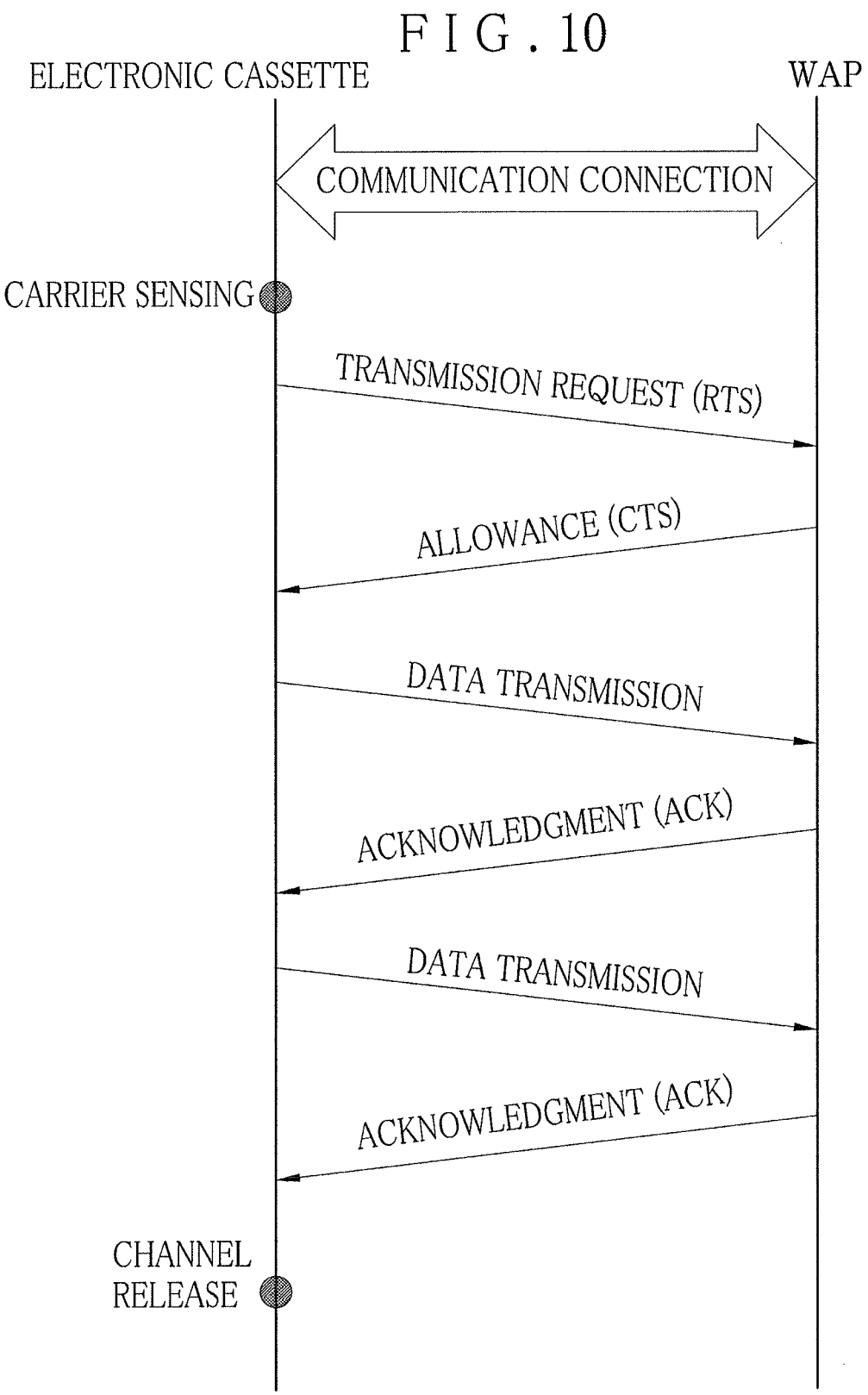
FIG. 10 is a timing chart illustrating a sequence of data communication.

In FIG. 10, a sequence of the data communication is illustrated. After the electronic cassette 16 becomes connected with the wireless access point device 36, the data communication is performed by the CSMA/CA method. At first, carrier sensing (detection of a carrier wave) is performed to check whether another portable terminal device is present locally for use a radio communication channel of an equal frequency. Assuming that the electronic cassette 16 receives radio waves of the equal frequency in the carrier sensing, a channel busy condition of a radio communication channel is detected, to stand by without starting generating radio waves for avoiding radio interference. Then the carrier sensing is continued. In case a radio communication channel of the equal frequency is released at another radio terminal (stops generating radio waves), generation of the radio waves is started. The electronic cassette 16 starts generating radio waves after another radio terminal releases a radio communication channel, because time of continuing occupation of a radio communication channel of the equal frequency is limited.

After the enablement of generating radio waves, at first the electronic cassette 16 transmits a transmission request to the wireless access point device 36 to request allowance (RTS or request to send) of transmission. The wireless access point device 36, assuming that reception is possible, sends back an allowance response (CTS or clear to send). Assuming that reception is impossible, the wireless access point device 36 does not send back an allowance response. The electronic cassette 16, assuming that no allowance response is received even at a lapse of a predetermined time, resends the transmission request. Assuming that an allowance response is received, the electronic cassette 16 starts data transmission, such as X-ray image.

Data is transmitted by a unit of a frame, namely, packet. In case the wireless access point device 36 receives the data, information ACK of acknowledgment is transmitted to the electronic cassette 16. An upper limit of a data size of data transmissible in one frame is predetermined. Data to be transmitted is divided in plural frames for data transmission of X-ray images and the like. Upon lapse of time of occupying radio waves in the electronic cassette 16, the data transmission (generation of radio waves) is interrupted, to release a radio communication channel. After the release, the carrier sensing is performed to repeat the steps described above.

Figure 11:
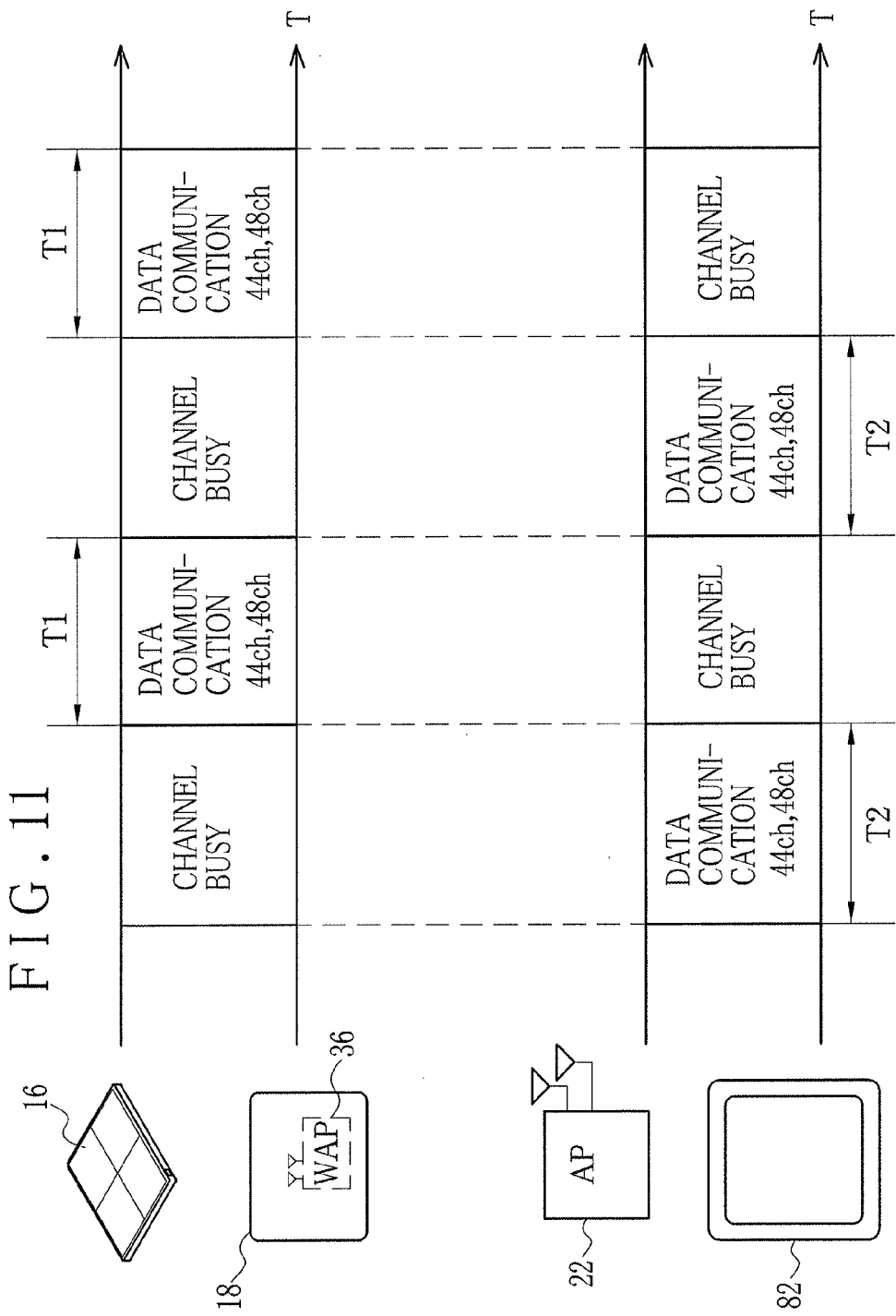
FIG. 11 is a timing chart illustrating operation of a radio communication channel in a time-sharing manner.

In case there is frequency overlap between radio communication channels of the wireless access point device 36 and the access point device 22 at 44th and 48th channels in the data communication of the CSMA/CA, each one radio communication channel is shared by the wireless access point device 36 and the access point device 22 in a time-sharing manner. See FIG. 11. For example, the wireless access point device 36 occupies the radio communication channel not continuously but intermittently in a period from a start to an end of the transmission of one X-ray image. In short, the radio communication channel is released with the intermittency during the period. Assuming that data communication is performed by another one of the access point devices 22, the radio communication channel having been released from the wireless access point device 36 for one time is occupied by the access point device 22. During the time period T2 of communication between the portable terminal device 82 and the access point device 22, communication is disabled between the electronic cassette 16 and the wireless access point device 36 because of a channel busy condition in which the radio communication channel is used by the other radio network node. In contrast, during the time period T1 of communication between the electronic cassette 16 and the wireless access point device 36, communication is disabled between the portable terminal device 82 and the access point device 22 because of a channel busy condition.

A data transfer rate of a data amount of transfer per unit time is measured as an effective data transfer rate inclusive of time of a channel busy condition. The data transfer rate decreases according to an increase in the channel busy condition. The data transfer rate of the electronic cassette 16 in FIG. 11 decreases according to an increase in the time T2 with a high level of the data amount of transfer of the portable terminal device 82 and the access point device 22, namely according to a decrease in the time T1. Also, the electronic cassette 16 communicates with the console unit 17 by use of the wireless access point device 36. A radio communication channel is shared by the electronic cassette 16 and the console unit 17 in a time-sharing manner. As a result, the electronic cassette 16, the console unit 17 and the portable terminal device 82 as three terminals share the single radio communication channel in the time-sharing manner, so that the data transfer rate of the electronic cassette 16 decreases considerably.

Figure 12:
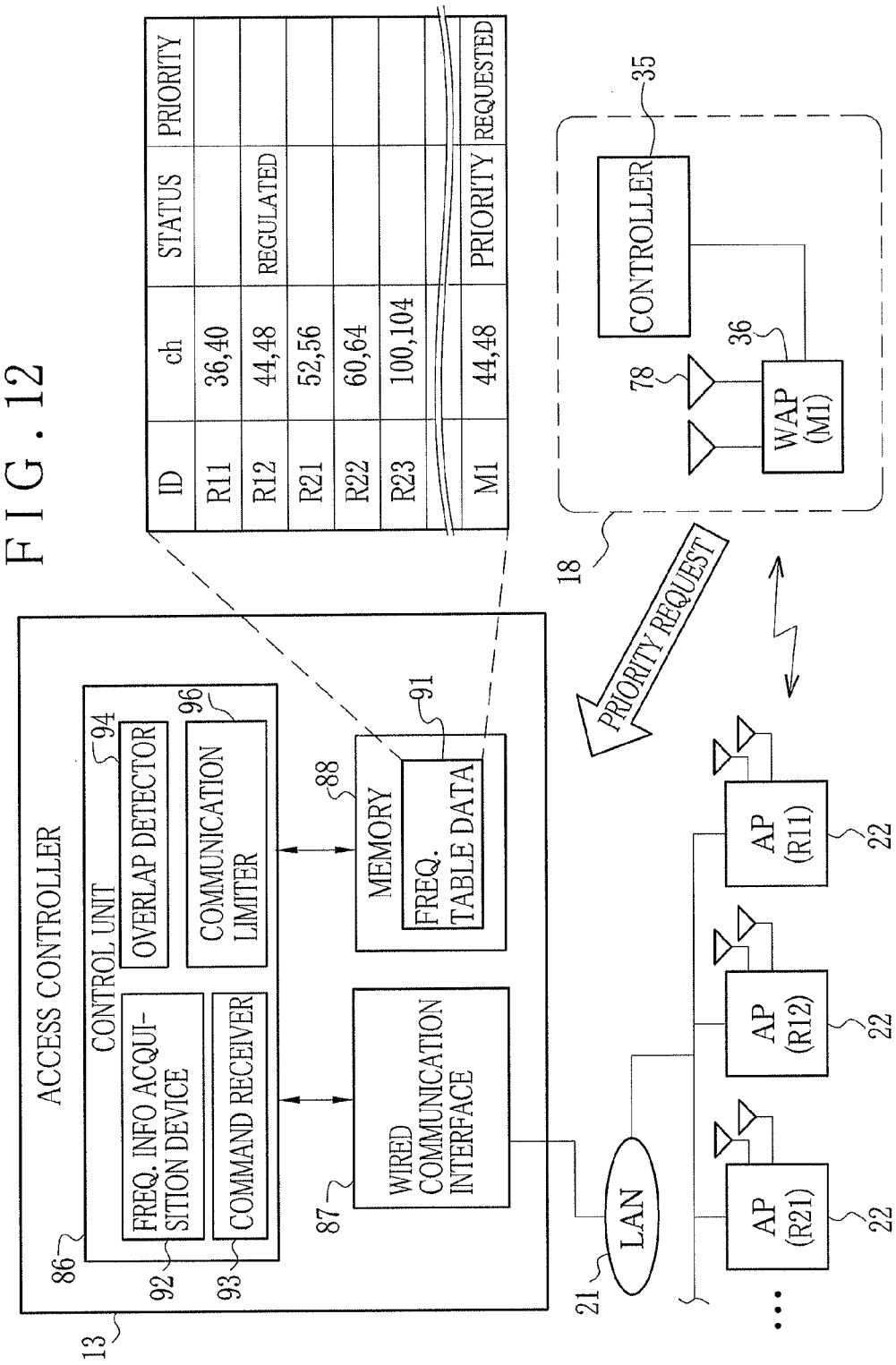
FIG. 12 is a block diagram schematically illustrating an access controller.

In FIG. 12, the access controller 13 includes a control unit 86, a wired communication interface 87 and a memory 88 as a storage medium. The control unit 86 controls various elements in the access controller 13. The wired communication interface 87 communicates with the local area network 21 in a wired manner. Frequency table data 91 (frequency information) is stored in the memory 88. Frequency information of a radio communication channel for use in the access point device 22 and the wireless access point device 36 is registered with the frequency table data 91. Various items are stored in areas of the frequency table data 91, including ID information of the access point device 22 and the wireless access point device 36, channel numbers of a radio communication channel used by the access point device 22 and the wireless access point device 36, status of communication, and existence of a priority request signal, and the like.

The control unit 86 includes a frequency information acquisition device 92, a command receiver 93 (receiving port) for a priority request signal, an overlap detector 94 and a communication limiter 96. The frequency information acquisition device 92 acquires a channel number of a radio communication channel for use in the access point device 22 through the wired communication interface 87 as frequency information. Frequency information of a radio communication channel used by the wireless access point device 36 is acquired through the access point device 22 and the wired communication interface 87. In the frequency information, IDs of the access point devices 22 and the wireless access point device 36 are included. The frequency information acquisition device 92 operates to register the acquired IDs and channel numbers in relevant areas of the frequency table data 91. In FIG. 12, signs R11, R12, R21 . . . and M1 for the access point devices 22 and the wireless access point device 36 denote data of IDs, which correspond to IDs registered in the frequency table data 91. Owing to the channel bonding in the access point devices 22 and the wireless access point device 36, two channels including 36th and 40th channels are assigned to each one of the access point devices 22 and the wireless access point device 36.

Various methods can be used for acquiring the frequency information. For example, an information request can be transmitted by the frequency information acquisition device 92 according to polling to the wireless access point device 36 and the access point device 22 for notifying the information request. Also, the wireless access point device 36 or the access point device 22 can notify the information request periodically at a predetermined interval of time.

The command receiver 93 receives a priority request signal from the control interface module 18 through the access point device 22. A time point of generating the priority request signal is a time point of detecting a start of irradiation of X-rays at the electronic cassette 16 as described above. The command receiver 93 receiving the priority request signal operates to store a request flag in an area of priority request signal. Also, the command receiver 93 notifies the overlap detector 94 of reception of the priority request signal.

Incase the priority request signal is received, the overlap detector 94 refers to the frequency table data 91 and checks whether there is one of the access point devices 22 with frequency overlap on a radio communication channel used by the wireless access point device 36 (ID=M1). In the example, the access point device 22 (ID=R12) uses 44th and 48th channels used by the wireless access point device 36, so that it is judged that the access point device 22 (ID=R12) with the overlap is present. The overlap detector 94 notifies the communication limiter 96 of a result of the judgement.

Assuming that the overlap occurs with the frequency of the wireless access point device 36 according to the result of the judgement from the overlap detector 94, then the communication limiter 96 transmits regulation information to the access point device 22 (ID=R12) of the target, to interrupt communication by the communication regulation. Specifically, the communication limiter 96 disables the access point device 22 of the target from transmitting a beacon signal and generating radio waves including a response to a portable terminal device (radio network node). Thus, the portable terminal device is disconnected from the access point device 22 of the target to disable the communication. As the beacon signal is not transmitted, new connection to the access point device 22 of the target is disabled. Consequently, the overlap of radio communication channels used by the wireless access point device 36 is removed owing to the stop of radio waves of the channel overlap of the wireless access point device 36.

For the communication regulation, the communication limiter 96 updates the status of the frequency table data 91. The communication limiter 96 operates to store regulation information for one of the access point devices 22 as a target of the regulation, and to store priority information for the wireless access point device 36 with priority. Also, the access controller 13 can notify the console unit 17 of the information of the communication regulation or ID information of an ID of the access point device 22 of the target. The console unit 17 displays the information of those states with the input screen 61 of FIG. 5.

After terminating image transmission from the electronic cassette 16 to the console unit 17, the control interface module 18 transmits an end flag to the access controller 13 to notify the end of the data transmission. The communication limiter 96 upon receiving the end flag transmits a release signal to the access point device 22 of the target for interrupting the communication regulation. Responsively, the access point device 22 restarts generating radio waves inclusive of the beacon signal.

Figure 13:
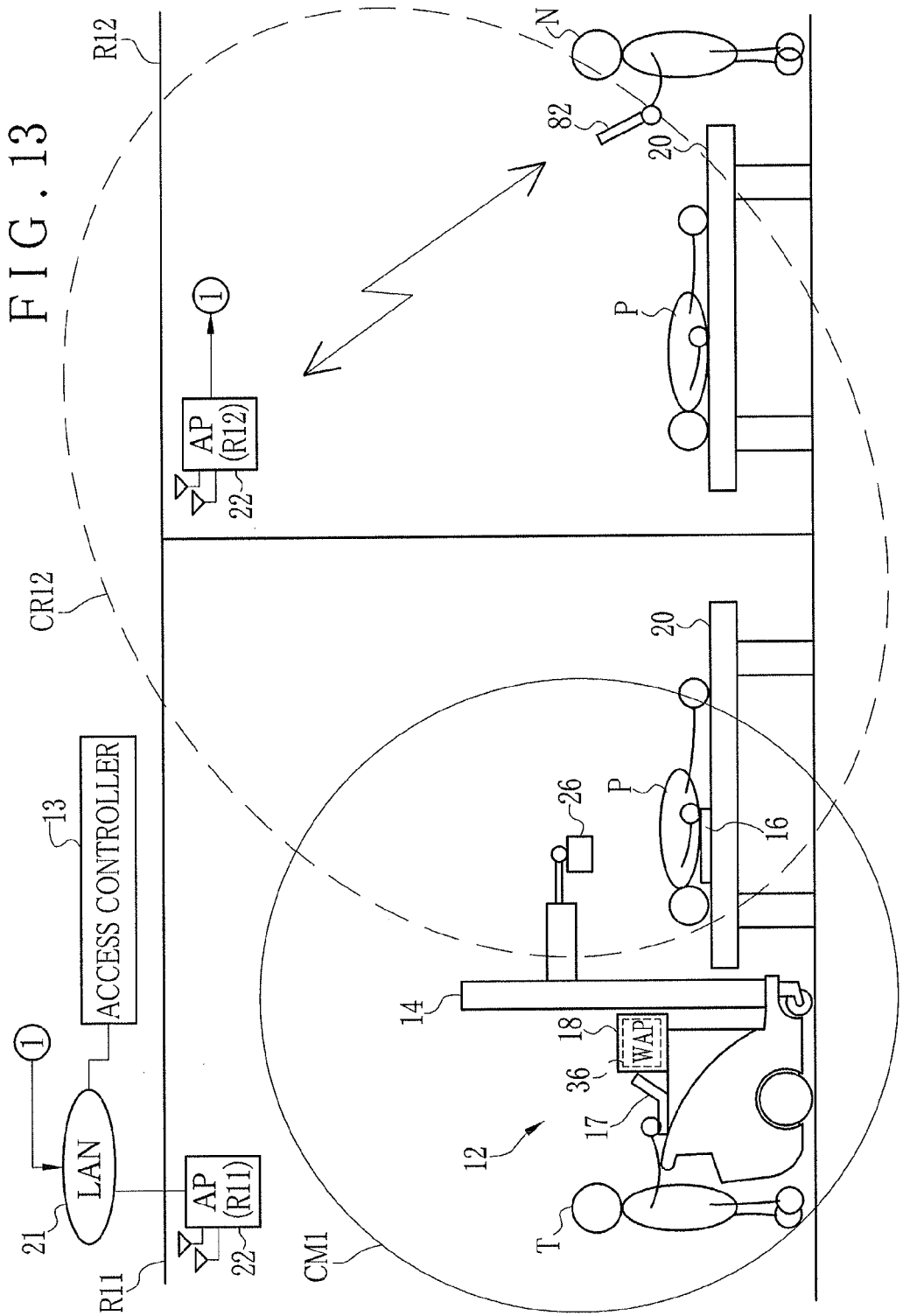
FIG. 13 is an explanatory view illustrating imaging in the in-patient care.
Figure 14:
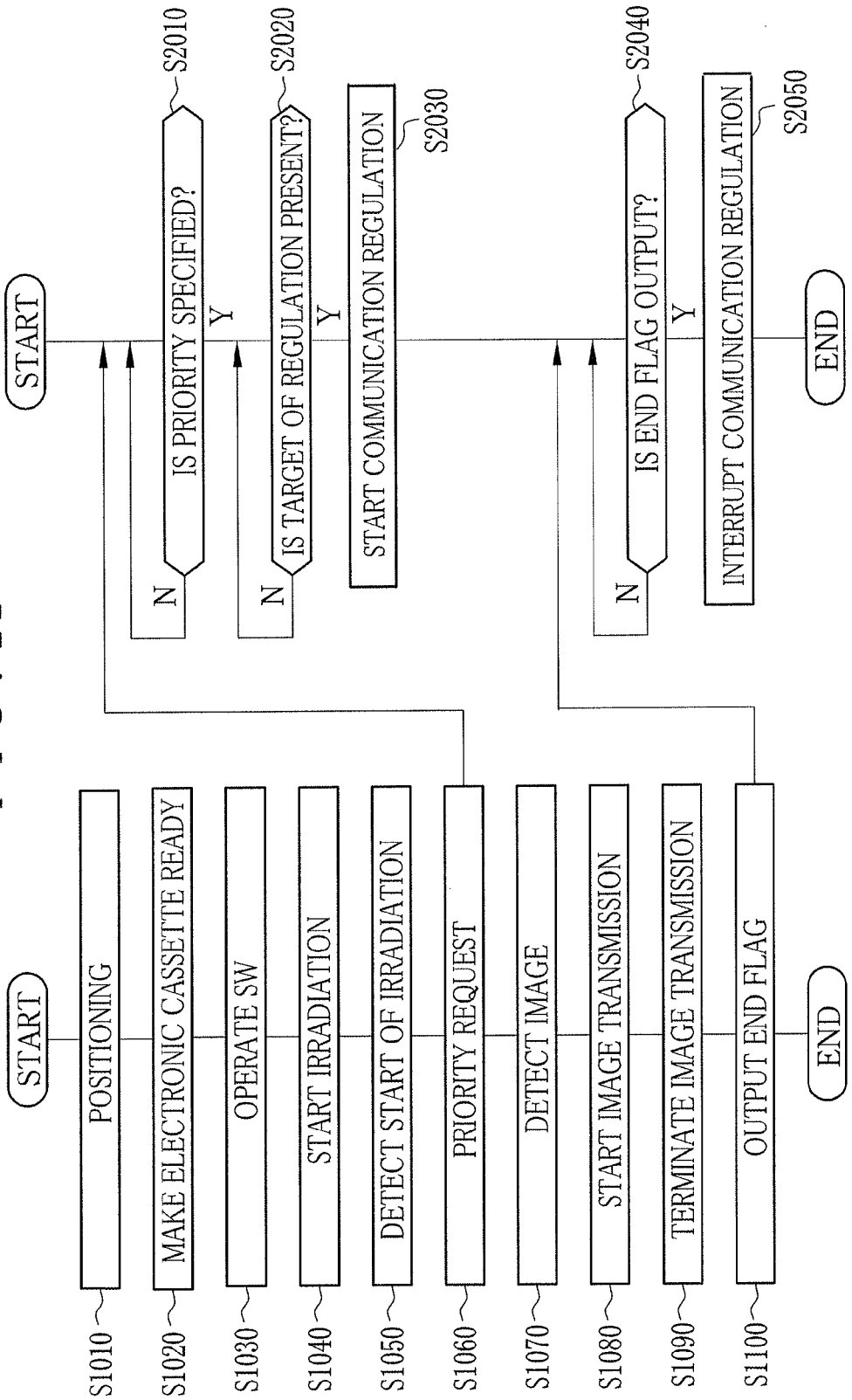
FIG. 14 is a flow chart illustrating communication regulation.
Figure 15:
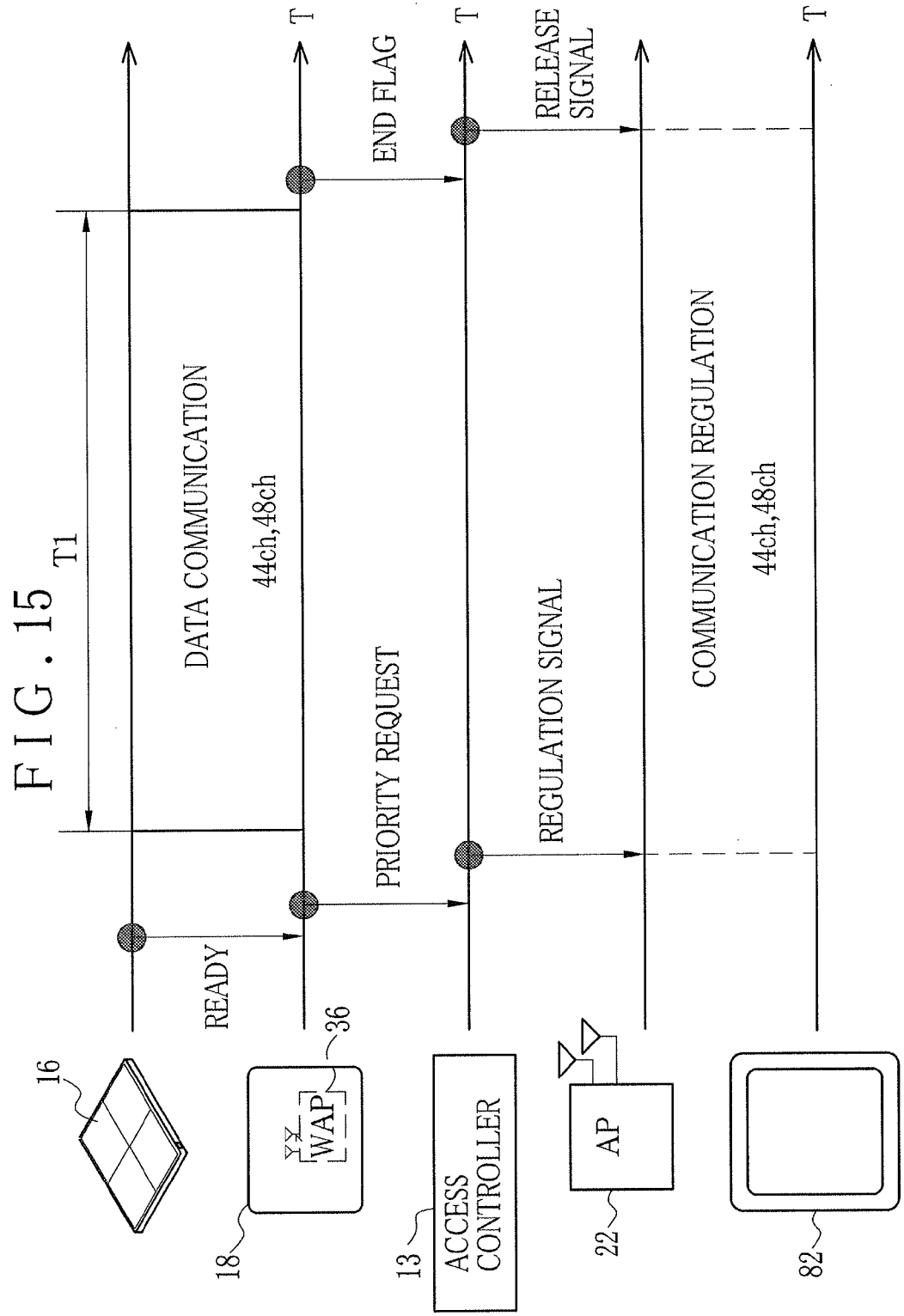
FIG. 15 is a timing chart illustrating the communication regulation.

The operation of the above-described construction is described now by referring to FIGS. 13-15. The operator T comes in the storage space 15 of FIG. 1 at first for imaging in the in-patient care, and places the X-ray imaging apparatus 12 on the medical cart 14, inclusive of the electronic cassette 16, the console unit 17 and the control interface module 18. The console unit 17 and the control interface module 18 are started up. The wireless access point device 36 starts transmitting a beacon signal in response to startup of the control interface module 18.

The console unit 17 receives the beacon signal, and becomes connected with the wireless access point device 36 in the connection sequence of the wireless communication connection similar to the electronic cassette in FIG. 7. Also, the wireless access point device 36 receives a beacon signal from the access point device 22 in the storage space 15. As the wireless access point device 36 operates in the client mode in relation to the access point device 22, the connection with the access point device 22 in the storage space 15 is made in the connection sequence similar to the electronic cassette in FIG. 7. The console unit 17 is manipulated by the operator T, accesses the RIS server 23 by use of the wireless access point device 36 of the control interface module 18, and receives an imaging request. The operator T checks the imaging request at the console unit 17, and identifies a hospital room for the in-patient care. It is possible to receive an imaging request at the console unit 17 by direct connection with the access point device 22 in the storage space 15 without use of the wireless access point device 36.

The operator T observes the position of the lock button 34 before starting running the medical cart 14, and confirms the engaged state of the lock mechanism 33 so as to prevent accidental shift of the X-ray source 26 during the movement. Assuming that the lock mechanism 33 is not engaged, he or she manipulates the lock button 34 for engagement. The medical cart 14 is moved from the storage space 15 toward rooms in the hospital facility 19. Also, the frequency information acquisition device 92 in the access controller 13 acquires frequency information periodically received from the access point device 22 and the wireless access point device 36. The frequency table data 91 is updated according to the acquired frequency information.

After entry of the medical cart 14 in the hospital room R11, the operator T prepares for imaging in FIG. 13. He or she reads the imaging condition according to the imaging request on the console unit 17. Then the electronic cassette 16 is started up. The radio communication interface 37 receives a beacon signal from the wireless access point device 36 of the control interface module 18, and becomes connected to the wireless access point device 36 in the connection sequence of FIG. 7. Thus, wireless communication connection is established through the wireless access point device 36 between the console unit 17 and the electronic cassette 16. He or she manipulates the console unit 17 to transmit the imaging condition to the electronic cassette 16. The electronic cassette 16 in response to the imaging condition sets a condition of signal processing in the sensor panel 41, for example, an input gain of the integrating amplifiers.

The operator T sets the irradiation condition of the X-ray source 26 according to the imaging condition by manipulating an input panel of the X-ray source apparatus 11 in the medical cart 14. Also, it is possible as illustrated in FIG. 3 wirelessly to transmit the irradiation condition from the console unit 17 to the X-ray source apparatus 11 for input. The control interface module 18 upon receiving a beacon signal from the access point device 22 (ID=R11) disposed in the hospital room R11 becomes connected to the access point device 22 (ID=R11) in the client mode as described above.

In FIG. 14, the X-ray source 26 and the electronic cassette 16 are positioned in the step S1010 in a manner suitable for an object of interest after setting the imaging condition. For example, the object of interest is located in the chest. In FIG. 13, the electronic cassette 16 is positioned between the hospital bed 20 and the body P of the patient lying on the hospital bed 20. The position of the electronic cassette 16 is adjusted for imaging of the chest. After the electronic cassette 16 is positioned, the X-ray source 26 is positioned. To this end, at first the lock mechanism 33 is released by operating the lock button 34 of the medical cart 14. The position and direction of the X-ray source 26 become changeable. The operator T moves the support arm 32, the support column 31 and the X-ray source 26 in the medical cart 14, and aligns the X-ray source 26 with an optical path of the electronic cassette 16 in relation to the position and direction of irradiation.

After the positioning, the detector button 72 (standby button) of FIG. 5 is manipulated in the input screen 61 of the console unit 17. The console unit 17 transmits an enable signal (standby signal) to the electronic cassette 16 through the wireless access point device 36 of the control interface module 18. The electronic cassette 16 in response to the enable signal becomes in the ready state (enabled state) in the step S1020. Then the detection sensors 56 of FIG. 4 are caused by the electronic cassette 16 to start detecting a start of irradiation.

The operator T sees the indicator 73 in the input screen 61 and visually confirms the ready state of the electronic cassette 16. He or she checks propriety in the posture of the body P of the patient, and manipulates the start switch 28 at a suitable time point in the step S1030. In response, the X-ray source 26 starts emitting X-rays in the step S1040. In the electronic cassette 16, the detection sensors 56 detect the start of irradiation in the step S1050.

The electronic cassette 16 transmits a start flag to the console unit 17 via the wireless access point device 36. In the control interface module 18, the controller 35 generates a priority request signal upon transmission of the start flag through the wireless access point device 36, so that the priority request signal is input to the access controller 13 in the step S1060. The electronic cassette 16 upon detecting the start starts the sensor panel 41 to operate for the storing, to start imaging in the step S1070.

The access controller 13 is ready to receive a priority request signal in the step S2010. The command receiver 93 receives the priority request signal in case the priority request signal is generated (yes in the step S2010). In response, the overlap detector 94 checks whether a target of the communication regulation is present in the step S2020. The overlap detector 94 refers to the frequency table data 91, and checks whether one of the access point devices 22 has frequency overlap on a radio communication channel for use in the wireless access point device 36. In the present example, frequency overlap occurs because 44th and 48th channels are commonly used by the wireless access point device 36 (ID=M1) and the access point device 22 (ID=R12) of the hospital room R12 next to the hospital room R11 with the medical cart 14. See FIGS. 12 and 13. Thus, the overlap detector 94 detects presence of a target of the communication regulation (yes in the step S2020).

In response to the result of evaluation of the presence of the target from the overlap detector 94, the communication limiter 96 transmits a command signal to the access point device 22 (ID=R12) of the target, to start the communication regulation in the step S2030. The communication limiter 96 updates the status of the frequency table data 91. The access point device 22 (ID=R12) of the target in response to the command signal stops generating radio waves and interrupts communication. Incase the portable terminal device 82 of a nurse N is connected to the access point device 22 (ID=R12)

of the target in the hospital room R12 in FIG. 13, the communication of the portable terminal device 82 is interrupted. A communication cell CR12 of the access point device 22 (ID=R12) overlaps on the communication cell CM1 of the wireless access point device 36. However, the communication cell CR12 disappears temporarily upon the interruption of the communication of the access point device 22 (ID=R12), as indicated by the broken line. Consequently, the wireless access point device 36 can use 44th and 48th channels with priority without radio interference with other radio network nodes.

The X-ray source 26 terminates irradiation upon lapse of the irradiation time. In case the detection sensors 56 detect the termination of the irradiation, the sensor panel 41 terminates the storing and reads an X-ray image. The X-ray image is stored to the memory 49. Then the radio communication interface 37 starts transmitting the X-ray image to the console unit 17 through the wireless access point device 36 in the step S1080. The transmission of the X-ray image is performed in the sequence of the data transmission in FIG. 10.

In FIG. 15, the access point device 22 or the portable terminal device 82 does not generate radio waves because of the communication regulation of the access point device 22. Carrier sensing and the channel release are repeated because the radio communication channel is shared in the time-sharing manner between the electronic cassette 16 and the console unit 17 during the image transmission of X-ray images from the electronic cassette 16 to the console unit 17 via the wireless access point device 36. However, the electronic cassette 16 and the console unit 17 do not detect radio waves from the portable terminal device 82 even upon performing the carrier sensing. A channel busy condition does not occur in relation to the image transmission of the portable terminal device 82 in the example of FIG. 11 without the communication regulation.

Therefore, the X-ray imaging apparatus 12 inclusive of the electronic cassette 16 and the console unit 17 is enabled to occupy one radio communication channel. Time of a channel busy condition is shorter than the example of FIG. 11, to increase the communication time T1 relatively. A data transfer rate of the X-ray image increases. As no radio interference occurs with other radio network nodes, no communication error or delay will occur. It is possible to transmit an X-ray image from the electronic cassette 16 to the console unit 17 in a short time reliably.

As described above, an operator T must form as many images as 50 or more per day by himself or herself. Should communication failure occur in a severe condition of short time, efficiency in the imaging may decrease considerably with his or her mental stress, because the total of numerous communication errors in the imaging may result in a considerable loss of time. However, it is possible to prevent decrease of the efficiency by effectively preventing communication errors or delay.

Communication of the access point device 22 of the target is interrupted temporarily by the communication regulation. Time of the communication regulation is comparatively short from detection of start of irradiation at the electronic cassette 16 until the end of the transmission of the X-ray image. Preferably, possibility of the communication regulation at a place of the medical cart 14 can be previously notified to a nurse N or medical service provider using the portable terminal device 82 for the in-patient care. The use of the communication regulation is sufficiently tolerable.

In case the image transmission from the electronic cassette 16 to the console unit 17 is terminated in the step S1090, the control interface module 18 transmits an end flag to the access controller 13 in the step S1100. The communication limiter 96 in the access controller 13 in response to the end flag (yes in the step S2040) transmits a release signal to a target node among the access point devices 22, to release this from the communication regulation (access regulation) in the step S2050. The access point device 22 starts generating radio waves again in response to the release signal.

Also, there are additional effects of the feature of the present invention. Assuming that communication errors or delay occurs frequently, time of generating radio waves from the X-ray imaging apparatus 12 becomes longer than required. Various wireless apparatuses are disposed in hospital rooms of the in-patient care, for example, a wireless vital monitor for monitoring a vital sign of a breathing rate, heart rate cardiac pulses and the like, and a pacemaker and the like. Radio waves from the X-ray imaging apparatus 12 are likely to influence to wireless apparatuses, so that reduction of a time period of generating the radio waves from the X-ray imaging apparatus 12 is considerably important. It is possible in the invention to minimize the time period of generating the radio waves from the X-ray imaging apparatus 12 by preventing communication errors or delay. Influence to other wireless apparatuses can be removed.

Assuming that a communication error occurs, it is likely that an X-ray image is lost, and that imaging of the same object must be carried out again in the case of the loss. However, such problems can be avoided by preventing the communication error. In general, a patient P is obliged to remain positioned in the posture until the X-ray image is viewed on the console unit 17 after irradiation of X-rays. However, stress of the patient P can be reduced by decreasing the waiting time for transmitting the X-ray image, because the time before checking the X-ray image can be decreased.

A battery is frequently used to drive the electronic cassette 16 for the purpose of the in-patient care. A time period of the image transmission is shortened by preventing communication errors or delay, so that power for use from the battery can be saved effectively. Total time of using the battery can be longer. Also, a size of the battery can be reduced owing to saving the power. The size reduction of the battery can decrease the weight of the electronic cassette 16. Accordingly, operation of the positioning can be facilitated by easy handlability of the electronic cassette 16.

In the above embodiment, the end flag from the control interface module 18 is transmitted via the access point device 22 to the access controller 13. The access point device 22 (ID=R11) disposed the nearest to the control interface module 18 is used for the transmission in the embodiment. However, it is likely that the access point device 22 (ID=R11) becomes a target of the regulation. A beacon signal is interrupted in the regulation of the embodiment. Assuming that the access point device 22 (ID=R11) is regulated for communication, the control interface module 18 cannot become connected to the access point device 22. Then the control interface module 18 sends the access controller 13 the end flag through one of the access point devices 22 different from the access point device 22 (ID=R11) in the regulation, for example, the access point device 22 (ID=R12).

Furthermore, it is possible in the access controller 13 to measure time and terminate the communication regulation upon a lapse of a reference period after the start of the communication regulation irrespective of an end flag. The reference period is predetermined by considering an average time required for image transmission from the electronic cassette 16 to the console unit 17. To this end, the control unit 86 in the access controller 13 measures elapsed time. The communication regulation can be terminated even assuming that the control interface module 18 cannot transmit the end flag to the access controller 13.

In the above embodiment, the control interface module 18 with the wireless access point device 36 transmits the priority request signal or end flag. However, it is possible for the console unit 17 to transmit the priority request signal or end flag to the access controller 13 by utilizing direct connection of the radio communication interface 38 to the access point device 22.

Second Preferred Embodiment

Although the communication of the access point device 22 of the target is interrupted for the purpose of communication regulation in the first embodiment, other methods can be used for the communication regulation.

Figure 16:
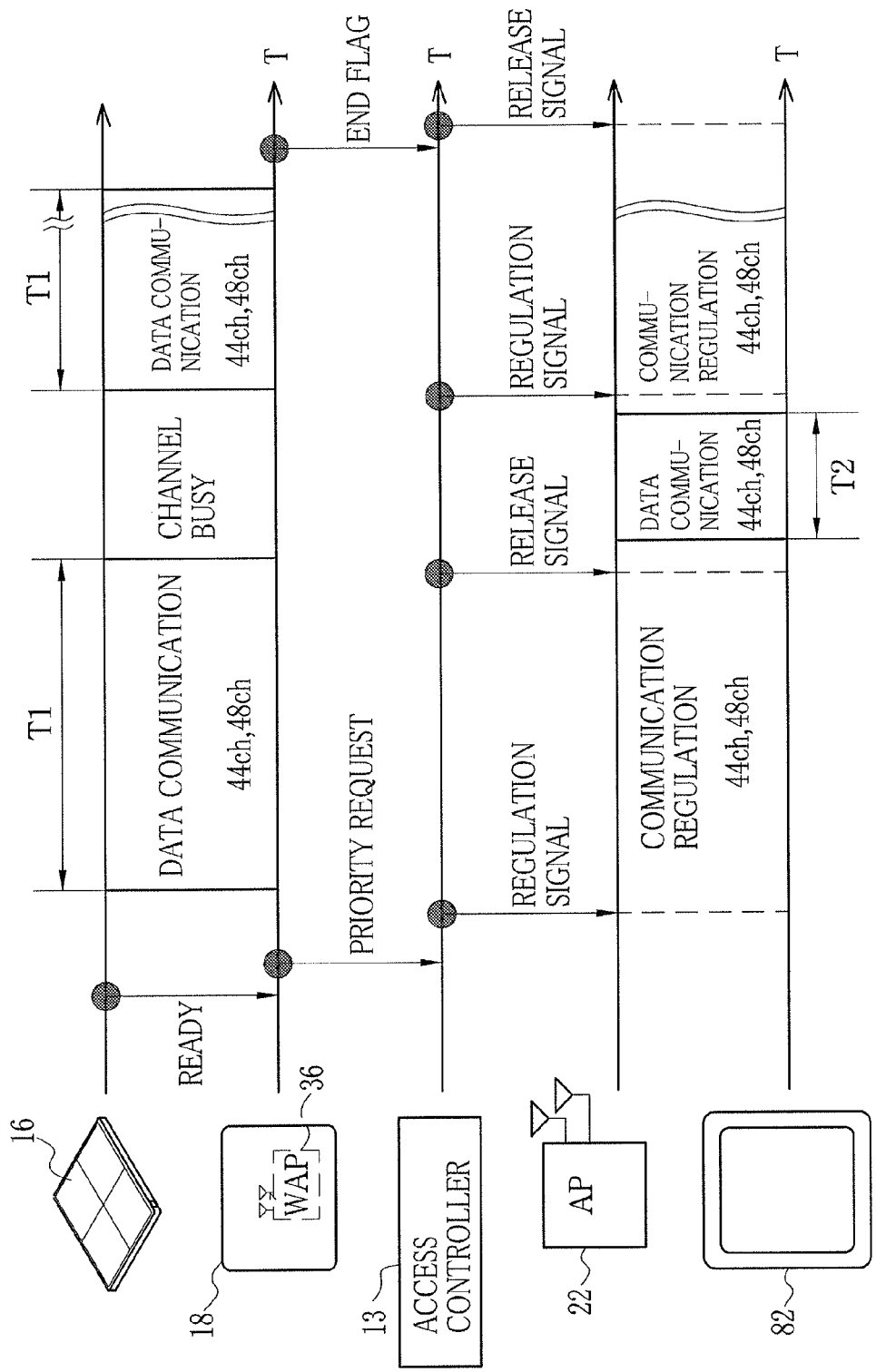
FIG. 16 is a timing chart illustrating another preferred example of communication regulation.

For example, a data transfer rate of the access point device 22 to be regulated can be limited. To this end, it is possible as illustrated in FIG. 16 to interrupt the communication of the access point device 22 intermittently in a period after the reception of the priority request signal at the access controller 13 until completion of transmitting an X-ray image. The access controller 13 repeatedly operates for outputting a regulation signal and a release signal to the access point device 22 to be regulated. An interval of outputting the regulation signal and release signal is so set that communication time T1 of the wireless access point device 36 is longer than communication time T2 of the access point device 22. Therefore, it is possible to limit the data transfer rate of the access point device 22 to be regulated in relation to the data transfer rate of the wireless access point device 36. It is possible according to the regulating method for the access point device 22 of the target to communicate, although its data transfer rate may become lower.

In the first and second preferred embodiments, the beacon signal is interrupted for the purpose of the communication regulation. However, a beacon signal may not be interrupted. See the connection sequence in FIG. 7. The access point device 22 continues transmitting the beacon signal, but simultaneously rejects wireless communication connection with the portable terminal device 82 without a response of allowance to a connection request from the portable terminal device 82. The portable terminal device 82 cannot start the data communication of FIG. 10 without connection between the portable terminal device 82 and the access point device 22. It follows that the communication between the access point device 22 and the portable terminal device 82 can be interrupted in this method.

Another method of interrupting communication of the access point device 22 is described. In the connection sequence of FIG. 7, the access point device 22 makes allowance to a connection request from the portable terminal device 82. Then in the data communication sequence of FIG. 10, the access point device 22 does not generate a response of allowance (CTS) to the transmission request (RTS). Thus, the data communication cannot be started even though the wireless communication connection of the portable terminal device 82 to the access point device 22 is possible. It is possible to interrupt communication between the access point device 22 and the portable terminal device 82 in a manner similar to the method of rejecting the connection.

In the method of communication regulation without interrupting the beacon signal from the access point device 22, no data communication of X-ray images is performed. However, the access point device 22 emits the beacon signal, so that the portable terminal device 82 in response to this generates a connection request intermittently. Even the beacon signal, connection request and the like may cause radio interference because of radio waves. However, a control frame (control packet) with the beacon signal and connection request for the transmission control has a smaller frame size (packet size) than a data frame (data packet) including data of an X-ray image, so that a period of generating radio waves is shorter. The transmission of data frames is disabled even in the method of communication regulation with allowed beacon signals from the access point device 22. Thus, a period of availability of a radio communication channel in the X-ray imaging apparatus 12 can be longer, to enable the use of the radio communication channel with priority.

As described heretofore, the method of the communication regulation is control of the access point device 22 by the access controller 13. Operation of the control command for controlling the access point device 22 with the access controller 13 may be supported as a standard command of the access point device 22, for example, interruption of the beacon signal. The above method can be realized advantageously without largely modifying a program, firmware or the like in the access point device 22 of the widely used type.

Furthermore, communication regulation of various types can be performed by adding or modifying programs in the access point device 22 or the portable terminal device 82, for example, changing a firmware in the access point device 22, or installing an application program for the communication regulation in the portable terminal device 82 to enable control with the access controller 13.

It is possible to limit communication load of data of transmission from the portable terminal device 82 by installing an application program in the portable terminal device 82 for communication regulation. To this end, the access controller 13 sends a regulation signal to the portable terminal device 82 for limiting the communication load for the communication regulation. For example, the portable terminal device 82 is allowed to transmit data of a relatively small data size, such as text data, and is inhibited from transmitting data of a relatively large data size, such as image data. Furthermore, it is possible to limit the communication load of data by adding or modifying programs in the access point device 22 for command of regulating sizes of data output by the access point device 22.

Also, the communication regulation can be announced previously. Before starting the communication regulation, the access controller 13 can notify the access point device 22 or the portable terminal device 82 of a start of the communication regulation, by adding or modifying a program in the access point device 22 or the portable terminal device 82. Upon receiving the announcement (initial flag) of the communication regulation, the access point device 22 or the portable terminal device 82 can operate for preparation for the communication regulation. As an example of the preparation, the access point device 22 or the portable terminal device 82 interrupts the data transmission at a suitable time point during the data transmission upon receiving the announcement (initial flag). Also, the access point device 22 or the portable terminal device 82 may be disabled from starting the transmission of data with a large data size after receiving the announcement.

Addition or modification of the programs in the access point device 22 or the portable terminal device 82 is advantageous because the communication regulation (access regulation) of various manners is possible. However, time and manual work are required for addition or modification of the programs in the access point device 22 or the portable terminal device 82 as disadvantages. This situation is remarkable typically with a higher number of devices of the access point device 22 and the portable terminal device 82. It is preferable as a method of the communication regulation to control only the access point device 22, for example, to stop transmitting the beacon signal of the access point device 22, or to reject connection of the portable terminal device 82 to the access point device 22.

Figure 17:
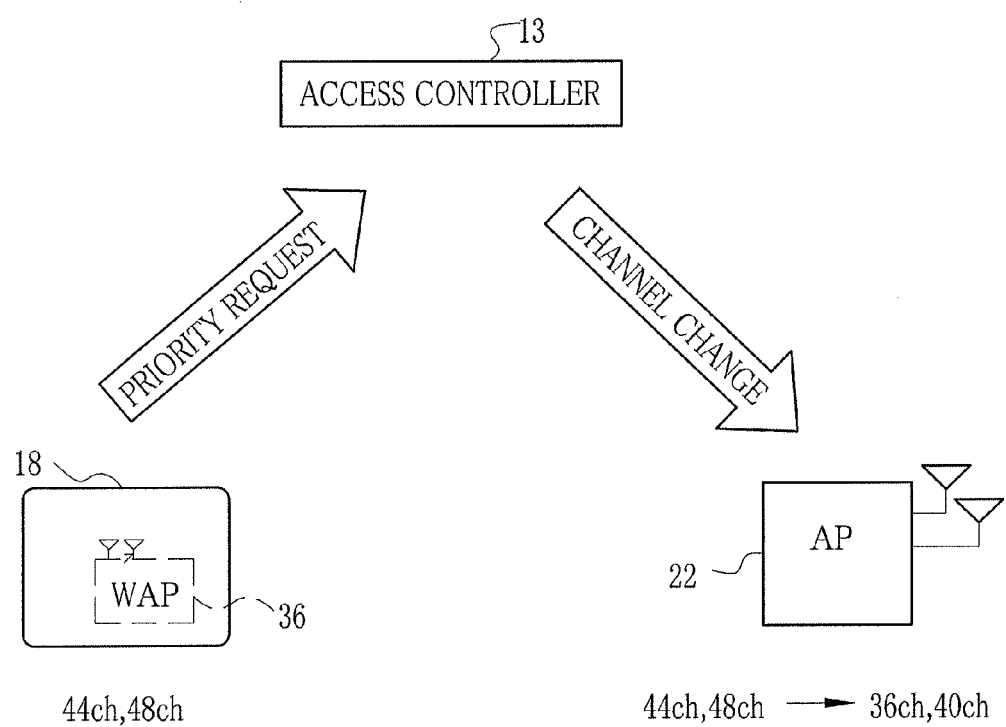
FIG. 17 is an explanatory view illustrating a change in the radio communication channel.

In FIG. 17, a method of the communication regulation may be a method of changing a frequency of a radio communication channel of the access point device 22 of the target. The access controller 13 upon receiving a priority request signal from the wireless access point device 36, the communication limiter 96 transmits a command signal to the access point device 22 of the target for changing a channel. In response to the command signal, the access point device 22 changes the frequency of a radio communication channel. For example, assuming that 44th and 48th channels of overlap of the wireless access point device 36 are used by the access point device 22 of the target of regulation, the channels are changed to 36th and 40th channels. Upon termination of the transmission of the X-ray image from the wireless access point device 36, the access controller 13 generates a command signal to the access point device 22 of the target to change back the channels, to interrupt the communication regulation.

Furthermore, it is possible selectively to change over the various methods of the communication regulation according to specifics of radio network nodes of target, and also to combine two or more of the various methods with one another suitably.

Also, a function of an automatic channel selection can be provided in each of the access point devices, in which available radio communication channels are searched locally (within a small distance) and automatically selected for use. The automatic channel selection is performed after startup of an access point device. At first, the access point device detects ambient radio waves, and detects a frequency of a currently used radio communication channel. A radio communication channel of an available frequency among selectable frequencies at the access point device is searched, to designate the radio communication channel (available channel) for use with the available frequency.

It is possible for the wireless access point device 36 in the control interface module 18 to perform the automatic channel selection. At the time of starting up the wireless access point device 36, the wireless access point device 36 searches an available channel by performing the automatic channel selection. Assuming that there is an available channel, the wireless access point device 36 selects this as a radio communication channel for use. Assuming that there is no available channel, the wireless access point device 36 generates a priority request signal and causes the access controller 13 to perform the communication regulation.

Third Preferred Embodiment

Another preferred embodiment is directed to restricting the access point device 22 of the target to be monitored. In the first embodiment, the access controller 13 acquires frequency information from all the access point devices 22 in the hospital facility 19, to control the communication environment by checking frequency overlap of the wireless access point device 36 of the X-ray imaging apparatus 12 in relation to all the access point devices 22 as target with the acquired frequency information. It is likely that all the access point devices 22 include a first one having frequency overlap of a radio communication channel of the X-ray imaging apparatus 12 but which is disposed without overlap of a communication cell (range of radio waves) of the X-ray imaging apparatus 12. However, the communication regulation for the first access point device is insignificant. Thus, it is preferable to restrict the target of the communication regulation to the access point devices 22 of which a communication cell is disposed with overlap of a communication cell of the X-ray imaging apparatus 12.

Figure 18:
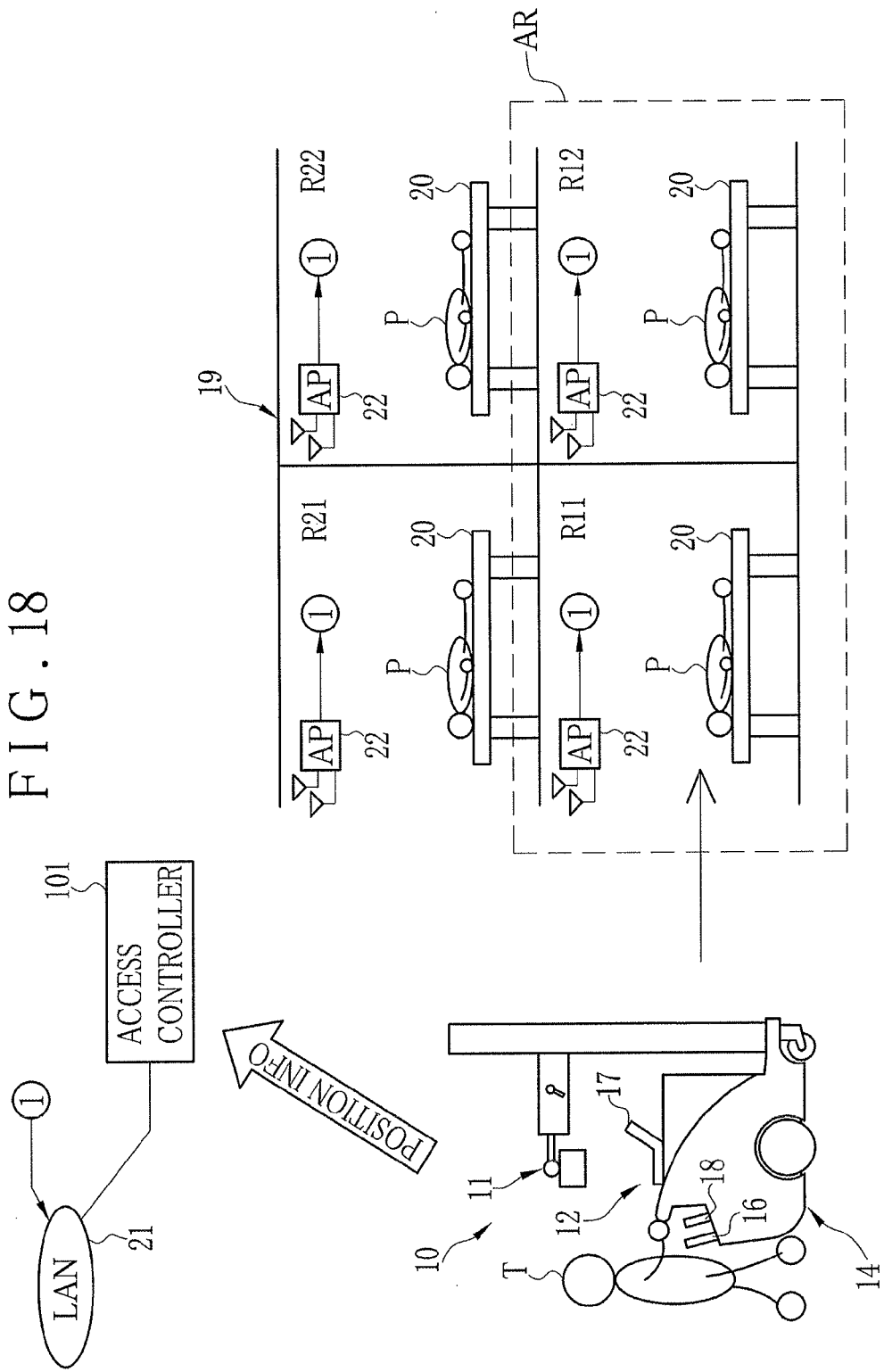
FIG. 18 is an explanatory view illustrating a preferred embodiment of restricting an access point device.
Figure 19:
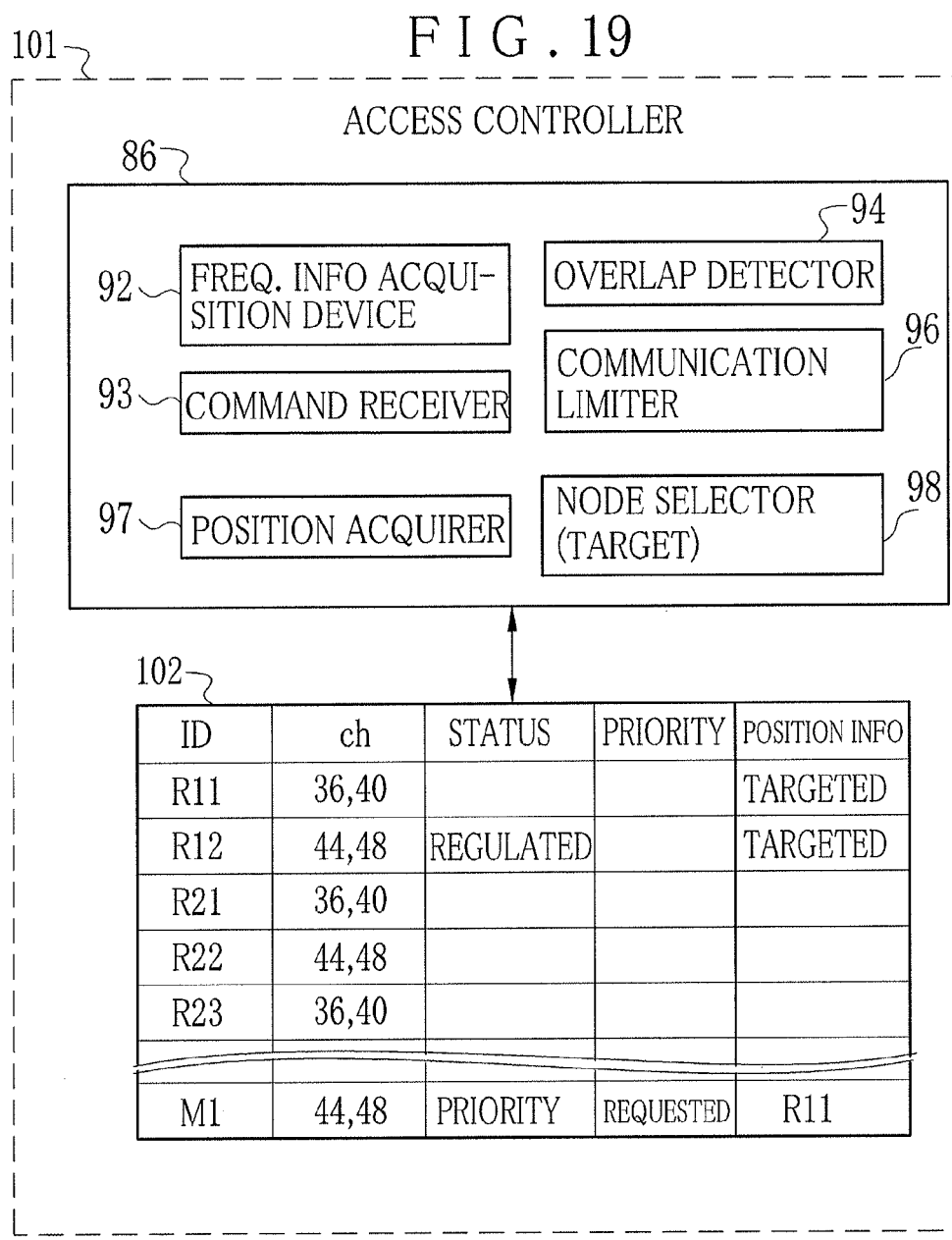
FIG. 19 is a block diagram schematically illustrating an access controller.

In FIGS. 18 and 19, an access controller 101 for communication access (communication environment) is illustrated, and detects presence of the access point device 22 near to the X-ray imaging apparatus 12 according to position information acquired from the X-ray imaging apparatus 12, so as to monitor only the detected one of the access point devices 22. For example, the X-ray imaging apparatus 12 is located in the hospital room R11 as illustrated in FIG. 18. Then a target of regulation is limited to the access point devices 22 in the hospital rooms R11 and R12 next to one another as indicated by the broken line AR. Assuming that a frequency of the access point devices 22 of the target overlaps on a frequency of the X-ray imaging apparatus 12, then the access controller 101 performs communication regulation to the access point devices 22 of the target.

In FIG. 19, the access controller 101 includes a position acquirer 97 and a node selector 98 or node determining unit, in addition to the construction of the access controller 13. The position acquirer 97 acquires position information through the local area network 21 from the wireless access point device 36 of the X-ray imaging apparatus 12. An example of the position information is an ID of the access point device 22 connecting for access of the wireless access point device 36 to the local area network 21. For example, the position information is R11 as an ID of the access point device 22 of the hospital room R11 in connection of the wireless access point device 36 to the access point device 22 of the hospital room R11. The X-ray imaging apparatus 12 transmits the position information at each time of a change in connection with the wireless access point device 36 among the access point devices 22.

The node selector 98 designates one of the access point devices 22 to be monitored according to the position information acquired by the position acquirer 97. In the example, the access point devices 22 in the hospital rooms R11 and R12 near to one another are designated as targets. At each time that the position information is updated, the node selector 98 designates one target node. Thus, a target node is changed according to movement of the X-ray imaging apparatus 12. A zone area of target nodes according to the position information can be suitably determined by considering a distance between the access point devices 22 and other information.

Frequency table data 102 as frequency information is a dataset of a relationship between the acquired position information, such as R11, and target information of the access point device 22 of the target. The position acquirer 97 and the node selector 98 operate to store the frequency table data 102. For example, the frequency of the access point device 22 (ID=R22) of the room R22 overlaps on that of the wireless access point device 36 (ID=M1) of the X-ray imaging apparatus 12. However, the access point device 22 (ID=R22) is not the target of the regulation, so that no communication regulation is performed. In the present embodiment, selection of the access point devices 22 can be minimized in view of influence of the communication regulation.

In case the X-ray imaging apparatus 12 is moved together with the medical cart 14, one of the access point devices 22 in connection with the wireless access point device 36 is changed. Position information is transmitted at each time of changing the access point device 22. The node selector 98 updates a target node of monitoring by evaluation at each time of transmission of the position information. Note that the position information of the embodiment is the ID of the access point device 22 connected with the wireless access point device 36. However, position information can be GPS information (global positioning system information) or the like. To this end, it is necessary for the X-ray imaging apparatus 12 to have a GPS function. Also, it is preferable previously to register room information in the access controller 101 through the console unit 17 for hospital rooms as destination of the in-patient care before starting the imaging.

Fourth Preferred Embodiment

Figure 20:
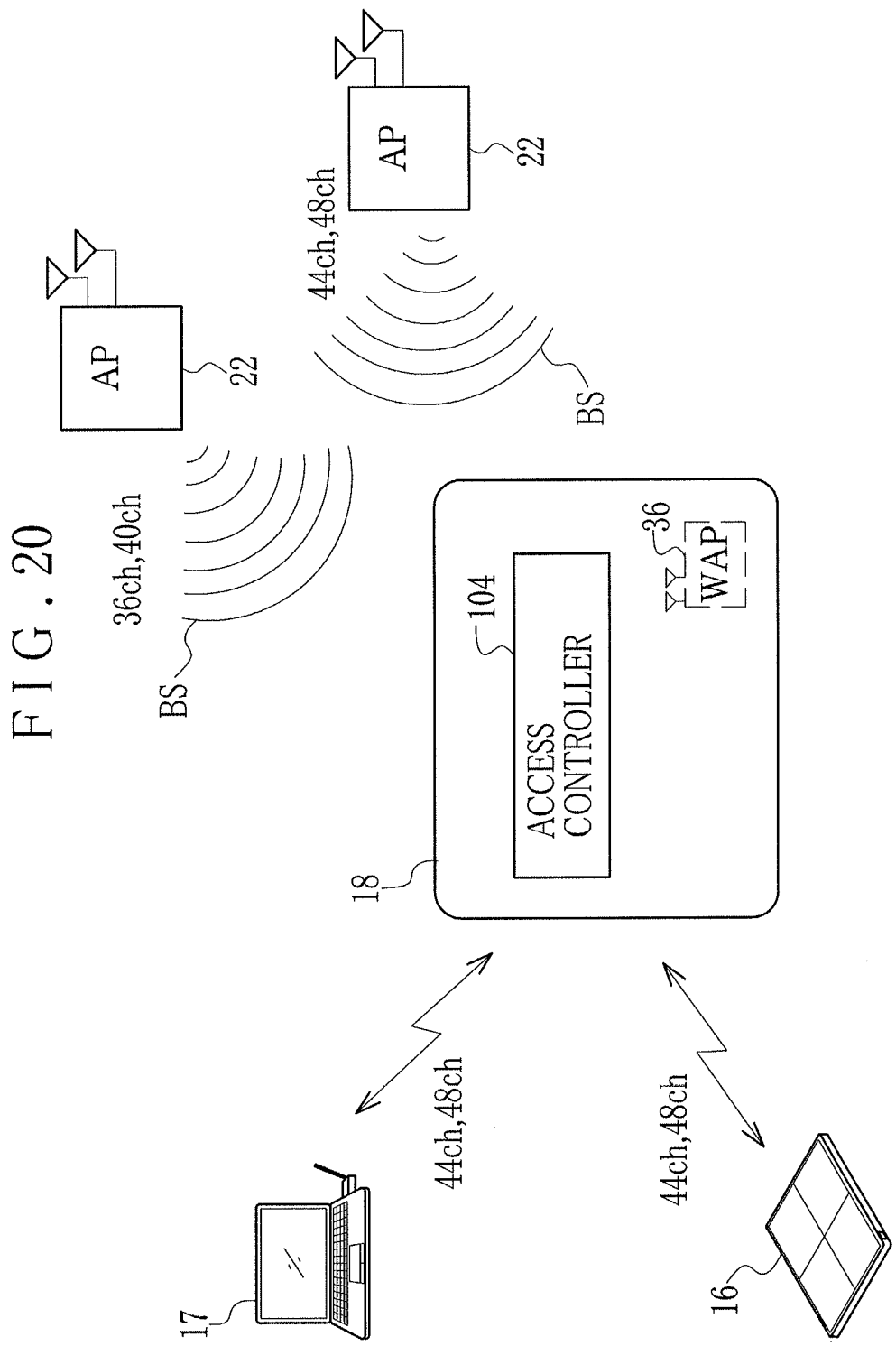
FIG. 20 is an explanatory view illustrating a preferred embodiment of a built-in access controller.
Figure 21:
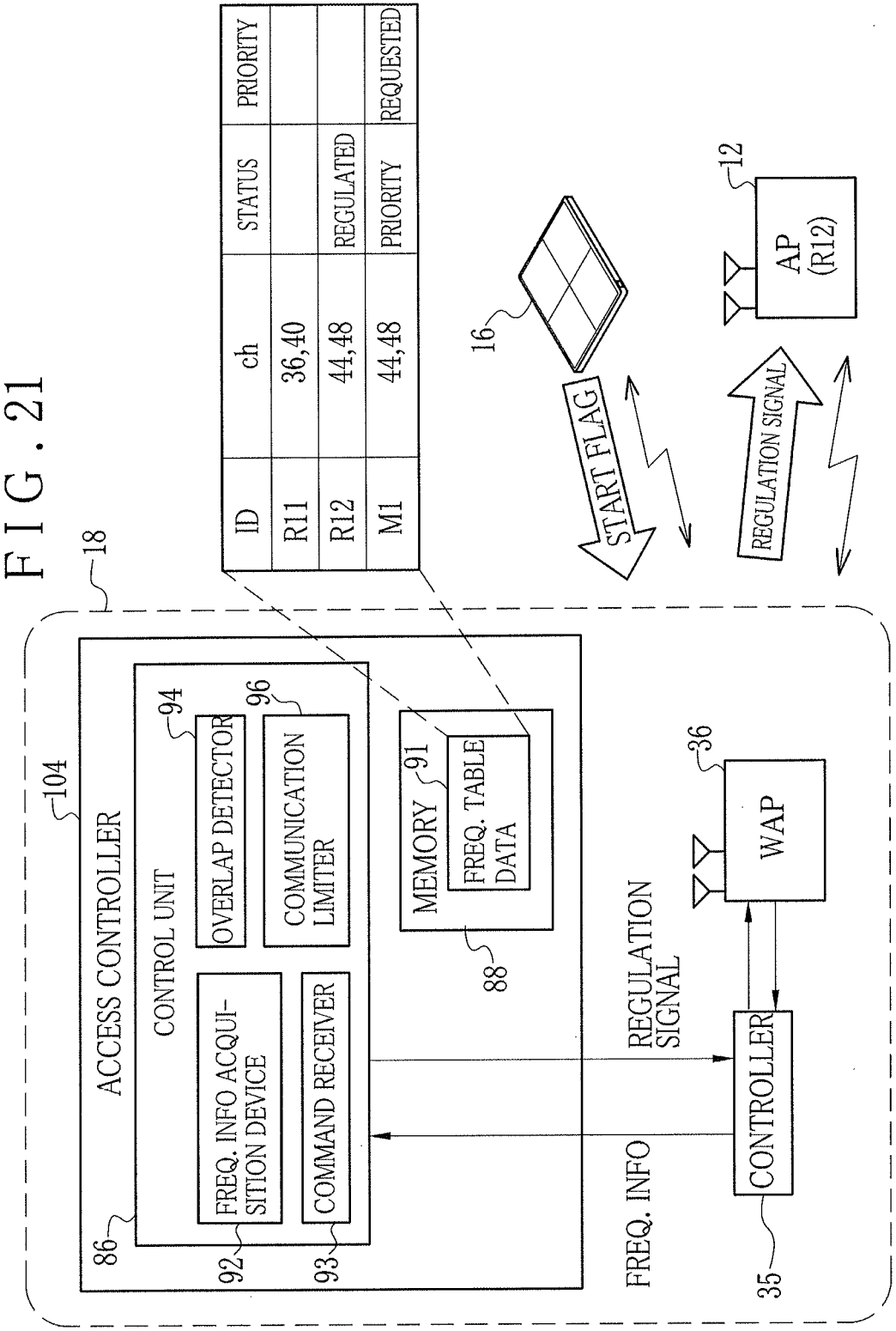
FIG. 21 is a block diagram schematically illustrating the access controller.

In contrast with the installed form of the access controller in the storage space 15, another preferred access controller 104 for communication access (communication environment) is mobile as a component assembled in the X-ray imaging apparatus 12. See FIGS. 20 and 21. For example, the access controller 104 is incorporated in the control interface module 18. The access controller 13 is repeated for partial elements in the access controller 104.

The wireless access point device 36 receives a beacon signal BS from one of the access point devices 22 being present locally. Frequency information of the beacon signal BS is input to the access controller 104 by the wireless access point device 36. The frequency information acquisition device 92 in the access controller 104 operates to store the frequency information from the wireless access point device 36 with the frequency table data 91. The access point device 22 near to the wireless access point device 36 is changed upon movement of the X-ray imaging apparatus 12, so that the frequency table data 91 is updated at each time of the change.

In a manner similar to the first embodiment, the controller 35 of the control interface module 18 generates a priority request signal according to an enable signal and response (ready flag) transmitted between the electronic cassette 16 and the console unit 17. The priority request signal is transmitted to the access controller 104. Then the overlap detector 94 refers to the frequency table data 91, and detects a target of regulation with frequency overlap. The communication limiter 96 performs communication regulation of the access point device 22 of the target according to the result of the detection.

The access controller 104 is moved according to the movement of the X-ray imaging apparatus 12 because of their combined form. The target of the communication regulation is only the access point device 22 in a range of reception of the beacon signal BS at the wireless access point device 36 in the X-ray imaging apparatus 12. Thus, the target of regulation can be minimized for the purpose in a manner similar to the third embodiment. Although the detection of the target requires the position information in the third embodiment, the target according to the fourth embodiment is only the access point device 22 being present within the range of reception of the beacon signal BS at the wireless access point device 36. This is an advantage in that no detection of a target according to position information is required.

In the present embodiment, the access controller 104 is incorporated in the control interface module 18. However, the access controller 104 can be incorporated in the console unit 17 or the electronic cassette 16. Also, the access controller 104 can be a mobile unit separate from the control interface module 18, the console unit 17 or the electronic cassette 16.

Fifth Preferred Embodiment

In the above embodiment, the time point of issuing the priority request signal is the time point of becoming in the ready state for imaging in the electronic cassette 16. In FIGS. 22-27, other preferred examples of the time point are illustrated. The time point of issuing the priority request signal can be any one of time points earlier than a start of the image transmission in one event of imaging.

Figure 22:
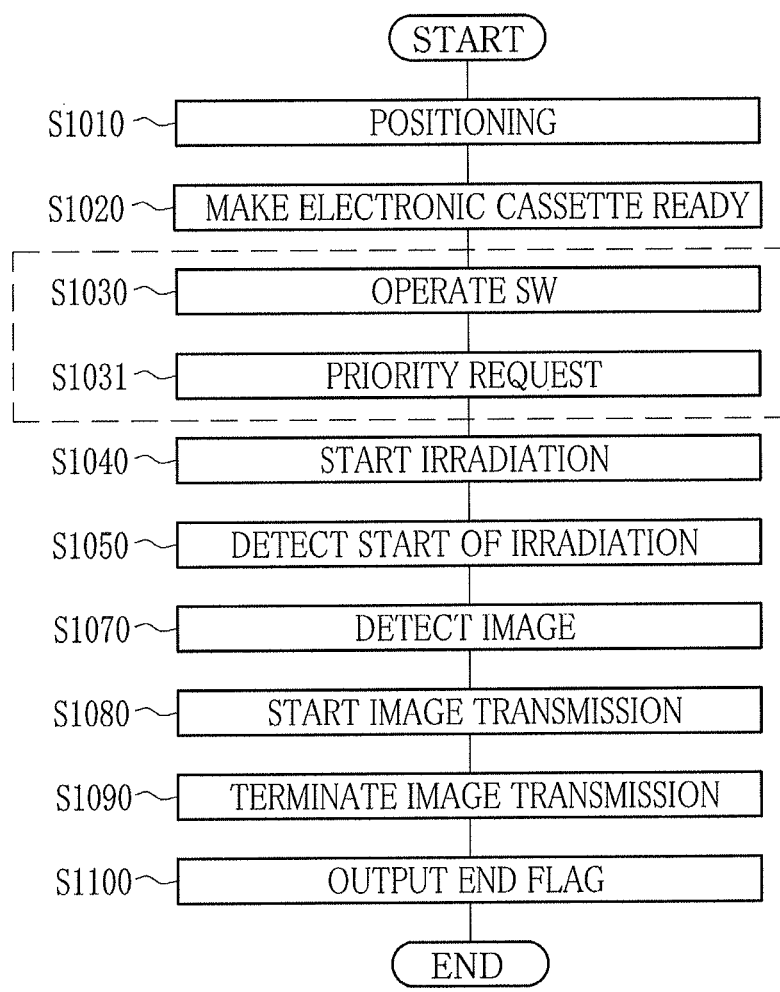
FIG. 22 is a flow chart illustrating generation of a priority request signal upon operating a start switch.

In FIG. 22, a priority request signal is generated upon manipulation of the start switch 28 of the X-ray source apparatus 11. The start switch 28 is operated in the step S1030, so that the source driver 27 of the X-ray source apparatus 11 of FIG. 1 outputs a start flag to the X-ray imaging apparatus 12 through the radio communication interface 29. The controller 35 in the control interface module 18 receives the start flag via the wireless access point device 36, and generates the priority request signal in the step S1031.

In comparison with the time point of detecting the start of irradiation in the electronic cassette 16 of FIG. 14, a time period after generating a priority request signal until image transmission is slightly longer according to FIG. 22. Thus, processing before starting the communication regulation can be performed with sufficient time in the access controller 13. It is possible reliably to start the communication regulation before the start of the image transmission.

Figure 23:
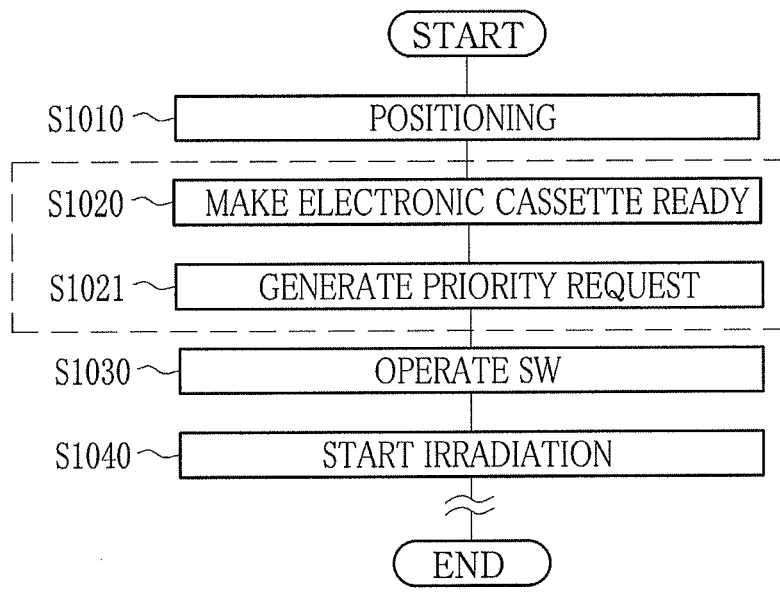
FIG. 23 is a flow chart illustrating generation of a priority request signal upon making the electronic cassette ready.
Figure 24:
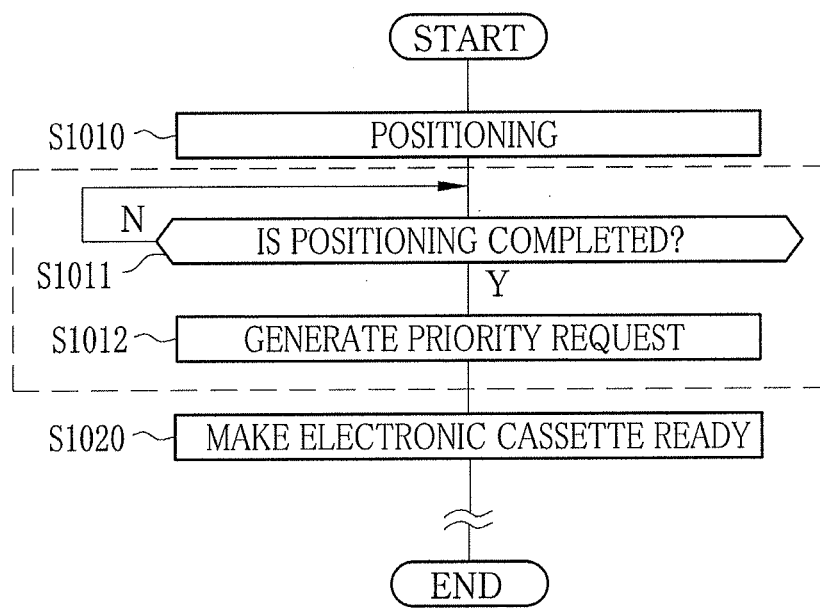
FIG. 24 is a flow chart illustrating generation of a priority request signal upon completion of positioning.

In FIGS. 23 and 24, an embodiment of keeping longer time for processing in the access controller 13 than FIG. 22 is illustrated. In FIG. 23, a time point of generating a priority request signal is a time point of setting the electronic cassette 16 in a ready state (enabled state). As described above, the electronic cassette 16 is set in the ready state by an enable signal (standby signal) from the console unit 17. In the controller 35, the wireless access point device 36 transmits the enable signal from the console unit 17 and also a response from the electronic cassette 16 to the console unit 17 upon receiving the enable signal. The controller 35 of the control interface module 18 judges that the electronic cassette 16 becomes set in the ready state by monitoring the signal transmitted by the wireless access point device 36, and generates a priority request signal in the step S1021.

FIG. 24 illustrates an example in which a priority request signal is generated at a time point of completion of the positioning. For example, a completion button is disposed in the input screen 61 of the console unit 17 for inputting a state of completion of the positioning. In response to manipulation of the completion button, the console unit 17 transmits a completion flag of the positioning to the control interface module 18. The control interface module 18 in response to the completion flag judges the completion of the positioning (yes in the step S1011). The controller 35 generates a priority request signal in the step S1012.

The completion button can be provided on the electronic cassette 16 or the medical cart 14. Otherwise, a detection sensor can be added for notifying completion of the positioning. For example, an acceleration sensor is provided on the electronic cassette 16. During the positioning, the posture of the electronic cassette 16 changes. However, the electronic cassette 16 is stationary upon completing the positioning. It is judged that the positioning is completed in case a stationary condition of the electronic cassette 16 is continued for a predetermined period by use of the acceleration sensor for detecting the stationary posture of the electronic cassette 16. Then the completion flag of the positioning is transmitted by the electronic cassette 16 to the control interface module 18.

Also, an ultrasonic transducer can be disposed on each of the electronic cassette 16 and the X-ray source 26 as a detection sensor, for transmission and reception of an ultrasonic signal. The ultrasonic transducers detect a state of positioning the electronic cassette 16 and the X-ray source 26 directed to one another, to recognize the completion of the positioning.

Figure 25:
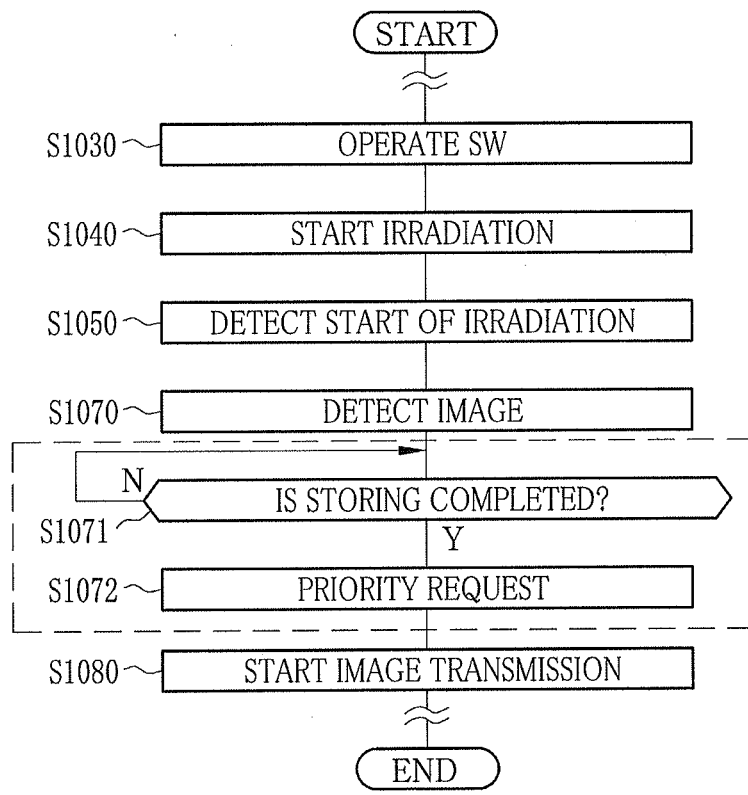
FIG. 25 is a flow chart illustrating generation of a priority request signal upon completion of the storing.

In FIG. 25, a priority request signal is generated at a time point of terminating the storing in the electronic cassette 16 (yes in the step S1071). The electronic cassette 16 transmits an end signal to the control interface module 18 as information of termination of the storing. The electronic cassette 16 starts the image transmission after terminating the storing and image readout. In the example, the control interface module 18 generates a priority request signal in the step S1072 after the storing until a start of the image readout. Thus, a time point of generating the priority request signal is shortly before the image transmission, so as to minimize time for the communication regulation. This feature is effective specially for a situation of considerably shortening the processing time from the generation of the priority request signal until the start of the communication regulation.

Figure 26:
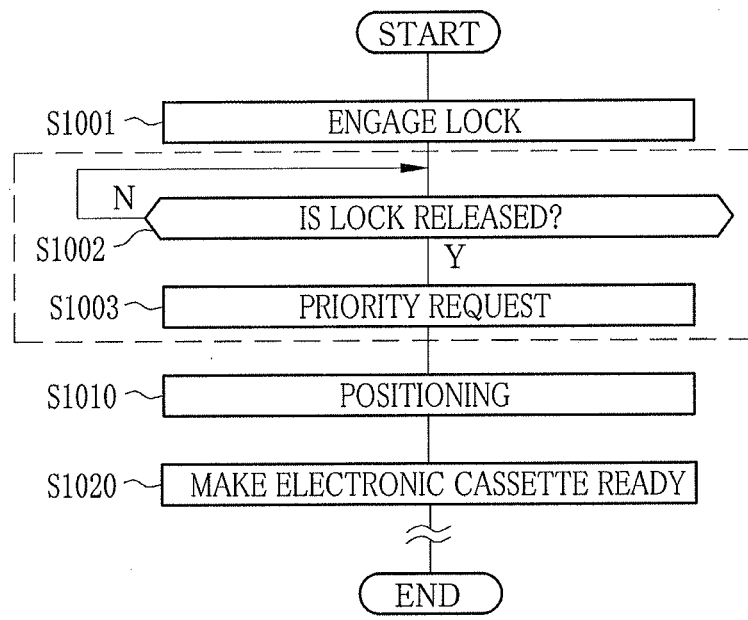
FIG. 26 is a flow chart illustrating generation of a priority request signal upon releasing a lock.

In FIG. 26, an embodiment of issuing a priority request signal upon releasing the lock mechanism 33 of FIG. 2 in the medical cart 14 is illustrated. For the imaging in the in-patient care, the medical cart 14 is run from the storage space 15 in the hospital facility 19. Before the start, the lock mechanism 33 is engaged in the step S1001. After reaching one of the hospital rooms, the lock button 34 is manipulated to release the lock mechanism 33 for positioning. The source driver 27 in response to release of the lock transmits an unlock signal to the control interface module 18 in the X-ray imaging apparatus 12 through the radio communication interface 29. The controller 35 of the control interface module 18 in response to the unlock signal in the step S1002 issues a priority request signal in the step S1003.

Figure 27:
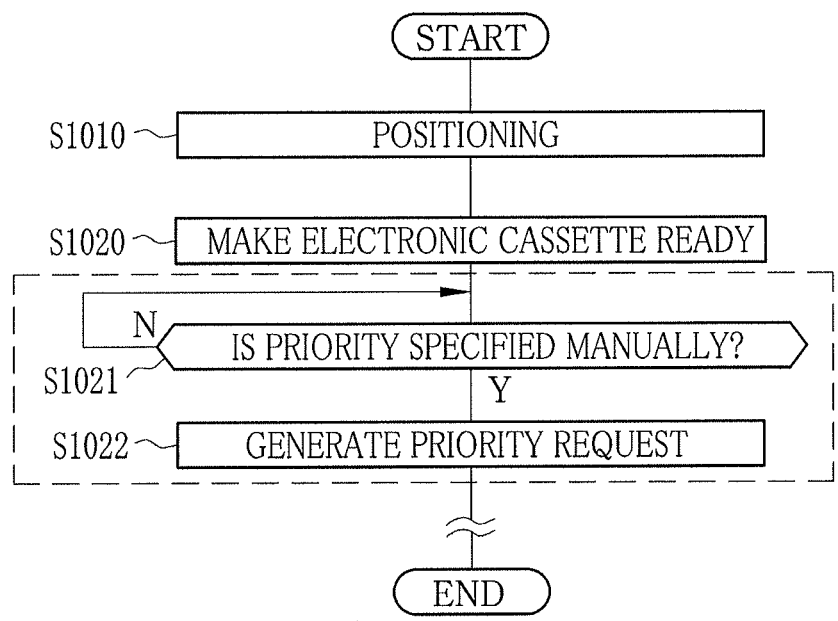
FIG. 27 is a flow chart illustrating generation of a priority request signal upon inputting the priority request signal.

In FIG. 27, an embodiment is illustrated in which a command button is disposed in the input screen 61 of the console unit 17 for specifying and instructing generation of a priority request signal. The console unit 17 generates the priority request signal in response to manipulation of the command button. For example, the operator T after the positioning operates the console unit 17 to set the electronic cassette 16 in the ready state in the step S1020. The command button of the console unit 17 is manually operated to transmit the priority request signal to the control interface module 18. The control interface module 18 recognizes the manual specifying of the priority by receiving information of the priority (step S1021), and generates the priority request signal.

Sixth Preferred Embodiment

Figure 28:
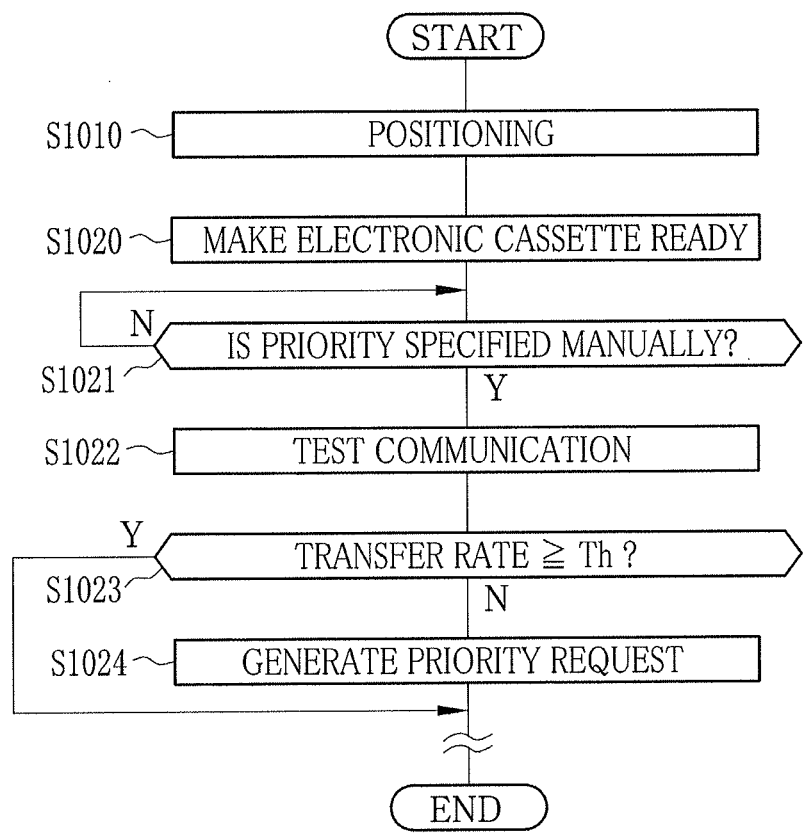
FIG. 28 is a flow chart illustrating communication test before a priority request signal.

FIG. 28 illustrates an embodiment in which communication regulation is performed according to a result of measurement of a data transfer rate of the X-ray imaging apparatus 12 by conducting communication test. At first, priority is specified in the step S1021 in FIG. 28. In the X-ray imaging apparatus 12, the electronic cassette 16 transmits sample data (dummy data) to the console unit 17 for the communication test in the step S1022. Assuming that the data transfer rate as a measurement result is equal to or more than a threshold Th, then the controller 35 in the control interface module 18 judges unnecessity of the communication regulation (yes in the step S1023). Then no priority request signal is generated. Assuming that the data transfer rate is less than the threshold Th, then the controller 35 judges necessity of the communication regulation (no in the step S1023), and generates a priority request signal. Consequently, necessity of the communication regulation is checked by evaluating the communication environment of the X-ray imaging apparatus 12. The communication regulation can be performed as required.

In the present embodiment, specifying the priority is combined with the communication test. However, a feature of each one of the above embodiments can be combined with the present embodiment. For example, the release of the lock according to FIG. 26 can be combined. In response to the release, the communication test is performed. A priority request signal is generated assuming that it is judged that the communication regulation is required according to a result of the measurement of the communication test.

Seventh Preferred Embodiment

Figure 29:
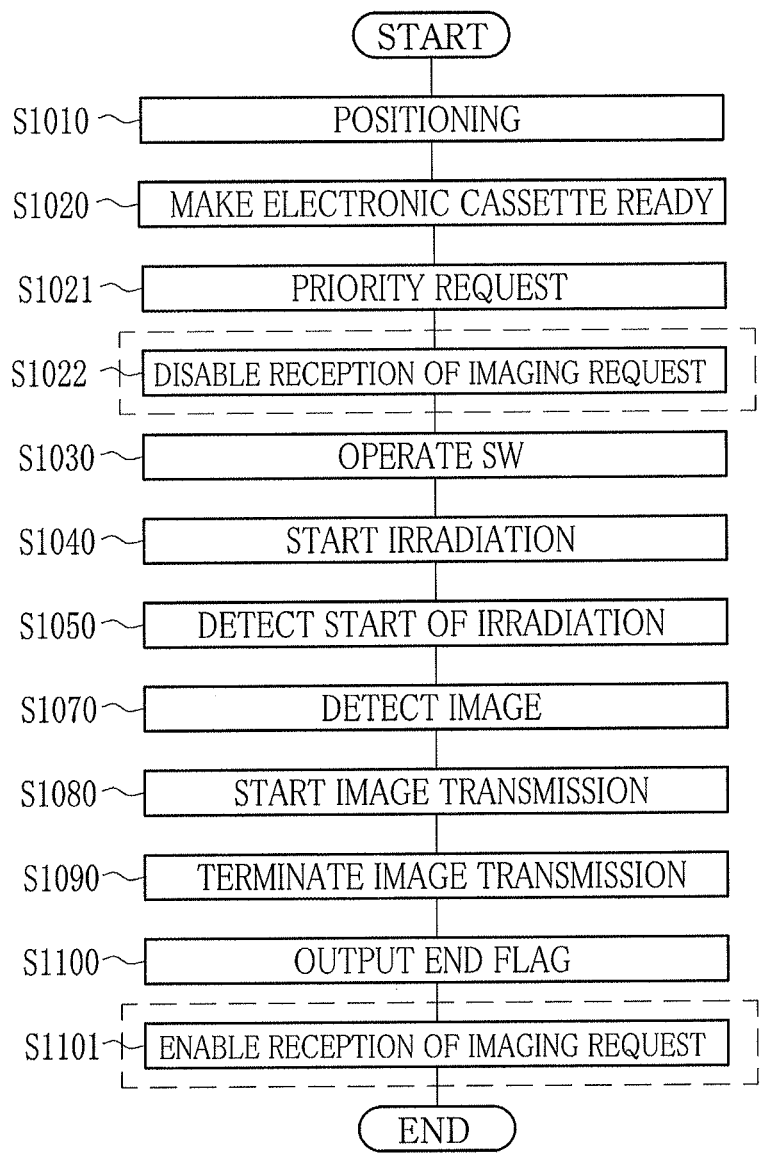
FIG. 29 is a flow chart illustrating interruption of receiving an imaging request.

In FIG. 29, communication other than transmission of X-ray image from the electronic cassette 16 is disabled after generation of a priority request signal in the X-ray imaging apparatus 12, for example, disabling of reception of an imaging request from the RIS server 23 to the console unit 17. It may be possible via the wireless access point device 36 to receive an imaging request by access of the console unit 17 to the RIS server 23. The console unit 17 and the electronic cassette 16 share one radio communication channel used by the wireless access point device 36 in a time-sharing manner. While the radio communication channel is used by the console unit 17, communication is disabled because a channel busy condition to the electronic cassette 16 is recognized. It is therefore preferable to disable communication other than the transmission of X-ray image in the course of transmitting X-ray images from the electronic cassette 16.

Incase a priority request signal is generated by the control interface module 18 in the step S1021 in FIG. 29, the console unit 17 interrupts reception of an imaging request in the step S1022. An end flag of the image transmission is transmitted to the access controller 13, before the reception of an imaging request is enabled again in the step S1101. Note that an example of communication other than image transmission from the electronic cassette 16 can be uploading of a previously obtained X-ray image from the console unit 17 to the image server 24. It is possible in the invention to interrupt the image transmission of such a previous image.

Also, it is possible for the console unit 17 to access the RIS server 23 or the image server 24 by direct connection to the access point device 22 without connection to the wireless access point device 36. Assuming that no frequency overlap occurs between a radio communication channel for an imaging request or image uploading at the access point device 22 and a radio communication channel between the console unit 17 and the wireless access point device 36, then problems do not occur in relation to the electronic cassette 16, inclusive of radio interference, drop in the data transfer rate in the time-sharing manner of the radio communication channel. However, influence in the delay of the processing is likely to occur because of simultaneous communication at the console unit 17 with plural radio network nodes of transmission. Thus, it is preferable to interrupt the communication in a manner other than the image transmission of X-ray images from the electronic cassette 16. In the technical field of channel bonding, the number of channels with possibility of bonding will increase in the future. In consideration of this, the number of the channels comes to decrease in one communication path in the course of the communication with plural radio network nodes. Consequently, it is preferable to interrupt the communication in a manner other than the image transmission of X-ray images for an additional purpose of ensuring the number of the channels with possibility of bonding.

Eighth Preferred Embodiment

Figure 30:
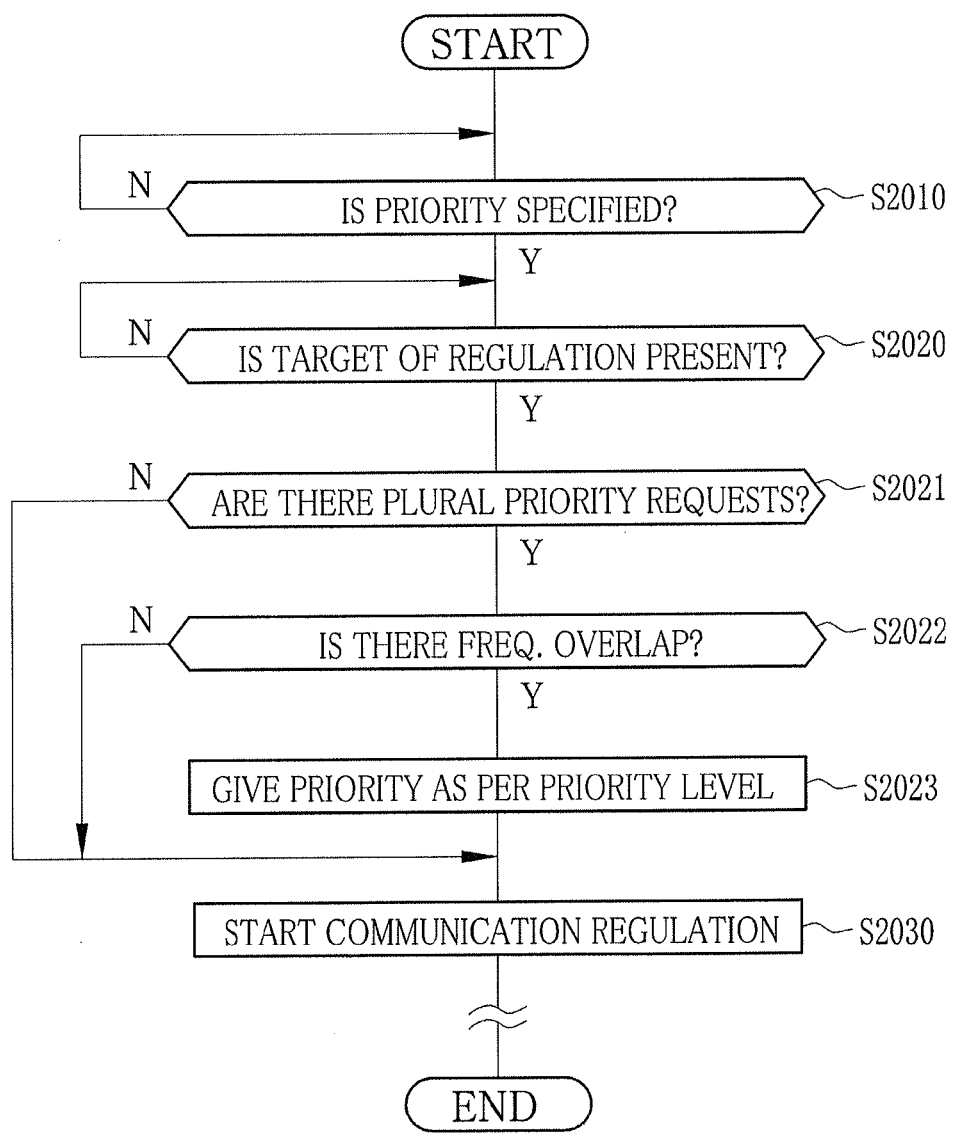
FIG. 30 is a flow chart illustrating consideration of priority levels.

In FIG. 30, a level of priority is considered to determine a target node in case there are plural priority request signals. For example, a plurality of the X-ray imaging apparatuses 12 output priority request signals simultaneously to the access controller 13. Level information of the level of priority is additionally associated by the X-ray imaging apparatuses 12 with priority request signals, such as high, medium and low levels, and transmitted to the access controller 13.

Assuming that only one priority request signal is received (no in the step S2021), then the access controller 13 starts the communication regulation (access regulation) of a target node with frequency overlap on the X-ray imaging apparatus 12 in the step S2030. Assuming that a plurality of priority request signals are received (yes in the step 2021), the access controller 13 checks whether overlap occurs between frequencies of a plurality of the X-ray imaging apparatuses 12 in the step S2022. Assuming that no frequency overlap occurs (no in the step S2022), then the access controller 13 starts the communication regulation of a target node with frequency overlap on each one of the X-ray imaging apparatuses 12. Assuming that frequency overlap occurs between the X-ray imaging apparatuses 12 (yes in the step S2022), then the access controller 13 starts the communication regulation of a target one of the X-ray imaging apparatuses 12 having lower priority, because the communication is enabled for one of the X-ray imaging apparatuses 12 with higher priority.

There is a possibility of urgently receiving an imaging request in the field of imaging in the in-patient care in a hospital. Priority of the urgent imaging request is higher than that of other normal imaging requests. Accordingly, the feature of the embodiment is effective for the urgent imaging request.

In the IEEE 802.11n, radio waves of the band of 5 GHz for radio communication channels are used in the above embodiments. However, radio waves of the band of 2.4 GHz can be used. Furthermore, other wireless LAN standards can be used, for example, the IEEE 802.11a, IEEE 802.11b, and IEEE 802.11ac of a new generation, and a wireless LAN standard different from the IEEE 802.11.

In the above embodiments, one radio communication channel is assigned to the wireless access point device 36 of the X-ray imaging apparatus 12. However, a plurality of radio communication channels can be assigned to the wireless access point device 36. The electronic cassette 16 and the console unit 17 can use radio communication channels different from one another.

In the above embodiments, the frequency information acquisition device 92 is incorporated in the access controller 13 for acquiring frequency information from the access point device 22 or the wireless access point device 36. However, the frequency information acquisition device 92 may not be used. Alternatively, it is possible previously to register frequency information with frequency table data in the access controller 13 for radio communication channels used by an access point of a hospital room and the X-ray imaging apparatus, typically in the case of an initially specified hospital room for imaging in the in-patient care.

In the X-ray imaging apparatus 12, the control interface module 18 with the wireless access point device 36 is separate from the electronic cassette 16 or the console unit 17. Also, the control interface module 18 (functional unit or intermediate network node) can be incorporated in the console unit 17 or the electronic cassette 16.

The priority request signal is generated by the X-ray imaging apparatus 12 in the above embodiments, but can be generated by the medical cart 14. To this end, a command button is additionally disposed on the medical cart 14 for generating the priority request signal.

In the X-ray imaging apparatus 12, a mode of the radio communication between the electronic cassette 16 and the console unit 17 can be the infrastructure mode with the wireless access point 36, and also an ad-hoc mode without using the wireless access point 36.

Unlike the X-ray imaging apparatus 12 and the medical cart 14 of the above embodiment, it is possible that the X-ray imaging apparatus is not communicable with the X-ray source apparatus. An X-ray imaging system of the present invention can be used in combination with the X-ray imaging apparatus 12, the access controller 13 and the X-ray source apparatus without having a communication interface, for example, a well-known radiation source apparatus for X-ray film, IP cassette and the like. However, it is easy to combine the electronic cassette with the X-ray source apparatus of the known type by use of the electronic cassette having a function of detecting irradiation of the above embodiments.

Examples of patients of the body P with limited mobility to be cared by use of radiographic imaging of the invention include all in-patients in hospital beds, for example, a bedridden patient who cannot stand or walk with a functional problem in legs, a patient in deep coma, and a patient in a complete bed rest for a reason of a disease, injury or surgery according to consultation of a physician or doctor.

The network for the radiographic imaging system of the present invention is the LAN or intranet. However, it is possible to use a well-known network for wireless communication connection. Also, the PACS (Picture archiving and communication system) can be used. However, it is highly preferable to manage access to the radiographic imaging system from terminal devices by use of security techniques for the purpose of proper management of medical information.

Also, it is possible to combine a known method of channel hopping and the like in the field of radio communication channels with the radiographic imaging system of the invention.

It is possible according to the invention to combine plural features of the embodiments with one another. Also, radiation in radiographic imaging in the invention can be gamma rays other than X-rays.

According an embodiment mode of the invention, the communication device is used for wireless communication connection to a communication network.

According an embodiment mode of the invention, the communication device is a radio network node.

According another embodiment mode of the invention, the communication device is an intermediate network node for connecting a radio network node to the communication network.

According an embodiment mode of the invention, the radiographic imaging apparatus is communicable by use of a communication network in wireless communication connection, and a storage device is connected to the communication network and stores the radiation image from the radiographic imaging apparatus.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiographic imaging system comprising:
   a radiographic imaging apparatus having an electronic cassette for forming a radiation image and wirelessly transmitting said radiation image; and
   an access controller for controlling communication access of said radiographic imaging apparatus, said access controller including,
      a storage medium for storing frequency information of a frequency of a first radio communication channel used by said electronic cassette for transmitting said radiation image, and of a frequency of a second radio communication channel used by a communication device different from said radiographic imaging apparatus and communicable wirelessly;
      a command receiver for receiving a priority request signal for priority of said first radio communication channel to said electronic cassette over said communication device before said electronic cassette starts transmitting said radiation image;
      an overlap detector for referring to said storage medium upon receiving said priority request signal, and checking presence of said communication device in which a radio communication channel of overlap of frequency on said first radio communication channel is used; and
      a communication limiter for operating in presence of said communication device with said overlap, and regulating said communication device in communication regulation while said electronic cassette transmits said radiation image.

2. A radiographic imaging system as defined in claim 1, wherein said communication regulation includes at least one of interruption of communication, limitation of a data transfer rate of transfer of data per unit time, and a change in said frequency of said radio communication channel used by said communication device.

3. A radiographic imaging system as defined in claim 1, wherein said access controller further includes a frequency information acquisition device for acquiring said frequency information of said second radio communication channel from said communication device.

4. A radiographic imaging system as defined in claim 3, wherein said second radio communication channel is used by at least one of a portable terminal device and an access point device for connecting said portable terminal device to a communication network by wireless communication connection.

5. A radiographic imaging system as defined in claim 4, wherein said communication limiter controls said access point device for said communication regulation.

6. A radiographic imaging system as defined in claim 4, wherein said frequency information acquisition device acquires said frequency information of said radio communication channel used by said access point device.

7. A radiographic imaging system as defined in claim 3, wherein said radiographic imaging apparatus further includes a console unit for receiving said radiation image from said electronic cassette, displaying said radiation image, and inputting a signal to said electronic cassette.

8. A radiographic imaging system as defined in claim 7, wherein said radiographic imaging apparatus has an intermediate network node for wireless communication connection between said electronic cassette and said console unit, and for wireless communication connection of said electronic cassette and said console unit to a communication network.

9. A radiographic imaging system as defined in claim 7, wherein while said electronic cassette transmits said radiation image, said radiographic imaging apparatus interrupts radio communication other than transmitting said radiation image.

10. A radiographic imaging system as defined in claim 7, wherein said console unit receives an imaging request, and interrupts reception of said imaging request while said electronic cassette transmits said radiation image.

11. A radiographic imaging system as defined in claim 3, wherein said radiographic imaging apparatus generates said priority request signal to said access controller at a predetermined time point before a start of transmission of said radiation image from said electronic cassette in one event of imaging.

12. A radiographic imaging system as defined in claim 11, wherein said predetermined time point is one of a time point of making said electronic cassette ready for imaging, a time point of completion of storing in said electronic cassette for detecting said radiation image, and a time point of manually inputting said priority request signal.

13. A radiographic imaging system as defined in claim 3, further comprising a radiation source apparatus, which includes:
   a radiation source for generating radiation; and
   a start switch for turning on and off said radiation source.

14. A radiographic imaging system as defined in claim 13, wherein said radiographic imaging apparatus is communicable with said radiation source apparatus, and said predetermined time point is a time point of receiving a signal of operation of said start switch from said radiation source apparatus.

15. A radiographic imaging system as defined in claim 13, wherein said electronic cassette detects a start of irradiation of said radiation source, and said predetermined time point is a time point of detecting said start of said irradiation in said electronic cassette.

16. A radiographic imaging system as defined in claim 13, wherein said radiation source apparatus comprises a mobile radiation source apparatus placed on a mobile cart.

17. A radiographic imaging system as defined in claim 1, wherein said priority request signal includes information of a priority level in relation to priority;
   said communication limiter performs said communication regulation according to said priority level upon receiving a plurality of said priority request signal.

18. A radiographic imaging system as defined in claim 1, wherein said access controller is incorporated in said radiographic imaging apparatus.

19. A radiographic imaging system as defined in claim 1, wherein said radiographic imaging apparatus measures a data transfer rate of said electronic cassette per unit time, and assuming that said data transfer rate is lower than a predetermined threshold, generates said priority request signal.

20. An access controller for controlling communication access of a radiographic imaging apparatus having an electronic cassette for forming a radiation image and wirelessly transmitting said radiation image, comprising:

a storage medium for storing frequency information of a frequency of a first radio communication channel used by said electronic cassette for transmitting said radiation image, and of a frequency of a second radio communication channel used by a communication device different from said radiographic imaging apparatus and communicable wirelessly;

a command receiver for receiving a priority request signal for priority of said first radio communication channel to said electronic cassette over said communication device before said electronic cassette starts transmitting said radiation image;

an overlap detector for referring to said storage medium upon receiving said priority request signal, and checking presence of said communication device in which a radio communication channel of overlap of frequency on said first radio communication channel is used;

a communication limiter for operating in presence of said communication device with said overlap, and regulating said communication device in communication regulation while said electronic cassette transmits said radiation image.

\* \* \* \* \*